(12) United States Patent
Cooperstock et al.

(10) Patent No.: US 8,066,372 B2
(45) Date of Patent: Nov. 29, 2011

(54) BINOCULAR VISION ASSESSMENT AND/OR THERAPY

(75) Inventors: Jeremy Cooperstock, Westmount, CA (US); Thang Long To, Montreal (CA); Jeff Blum, Montreal (CA); Robert F. Hess, Montreal (CA); Benjamin Simon Thompson, Auckland (NZ)

(73) Assignee: McGill University, Montreal, Quebec (CA)

( * ) Notice: Subject to any disclaimer, the term of this patent is extended or adjusted under 35 U.S.C. 154(b) by 0 days.

(21) Appl. No.: 12/772,162

(22) Filed: Apr. 30, 2010

(65) Prior Publication Data

US 2010/0283969 A1 Nov. 11, 2010

Related U.S. Application Data

(63) Continuation-in-part of application No. 12/528,934, filed as application No. PCT/IB2008/054365 on Oct. 23, 2008.

(60) Provisional application No. 60/981,859, filed on Oct. 23, 2007, provisional application No. 60/987,078, filed on Nov. 11, 2007.

(51) Int. Cl.
*A61B 3/08* (2006.01)
*A61B 3/00* (2006.01)

(52) U.S. Cl. ..................... 351/201; 351/200

(58) Field of Classification Search ........... 351/200–246
See application file for complete search history.

(56) References Cited

U.S. PATENT DOCUMENTS

| | | | |
|---|---|---|---|
| 5,309,185 A | 5/1994 | Harper | 351/202 |
| 5,764,340 A | 6/1998 | Hofeldt | 351/201 |
| 5,912,650 A * | 6/1999 | Carollo | 345/7 |
| 6,708,109 B1 * | 3/2004 | Pradhan et al. | 701/207 |
| 6,851,807 B2 | 2/2005 | Holdeman | 351/203 |
| 7,290,878 B1 * | 11/2007 | Hofeldt | 351/201 |

FOREIGN PATENT DOCUMENTS

| | | |
|---|---|---|
| DE | 733 759 | 4/1943 |
| EP | 0 578 236 A1 | 1/1994 |
| JP | 2006-122661 A | 5/2006 |
| WO | WO 96/27324 A1 | 9/1996 |
| WO | WO 03/092482 A1 | 11/2003 |
| WO | WO 2008/070683 A1 | 6/2008 |

OTHER PUBLICATIONS

McColl, et al., "Stereodeficient Subjects Demonstrate Non-Linear Stereopsis", Vision Research 40 (2000) 1167-1177, Elsevier Science Ltd., Montreal, Canada, Jan. 23, 2007.
Hess, et al., "Binocular Influences on Globarl Motion Processing in the Human Visual System", Vision Research 47 (2007) 1682-1692, Elsevier Science Ltd., Montreal, Canada, Nov. 8, 1999.

* cited by examiner

*Primary Examiner* — Mohammed Hasan
(74) *Attorney, Agent, or Firm* — Law Offices of Paul E. Kudirka

(57) ABSTRACT

This invention is a game platform for the assessment and/or treatment of disorders of binocular vision, such as amblyopia. The game content is devised to maximize the possible therapeutic effects by leveraging advanced research in ophthalmology, as well as advanced display technology to render images independently to each eye. In particular, the game content engages both eyes at different levels of difficulty, forcing an amblyopic eye to work harder to regain its performance in the visual system. The invention herein described provides a mobile device, capable of interaction with an eye care specialist, for the assessment/treatment of binocular vision using innovative mechanisms for ensuring proper use thereof.

16 Claims, 25 Drawing Sheets

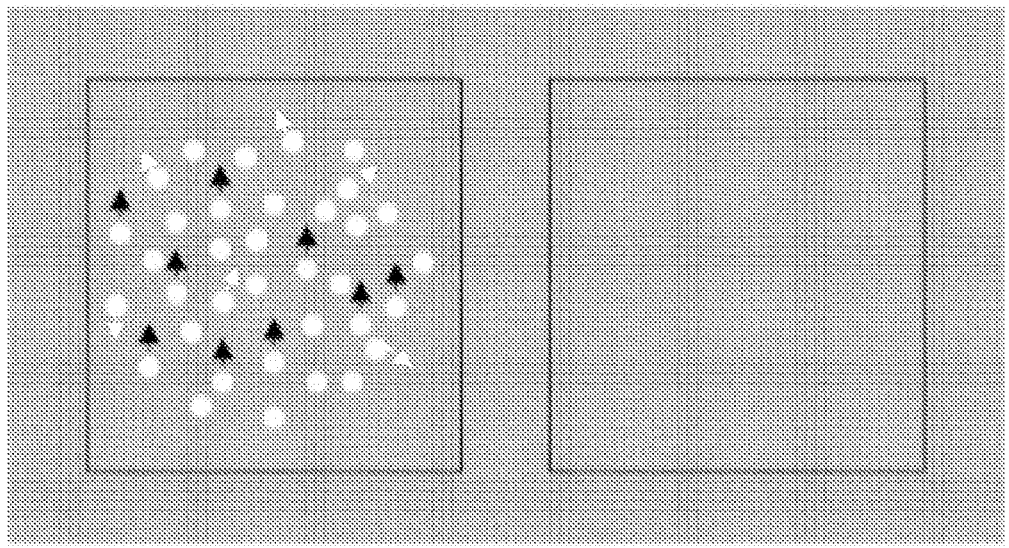
Figure 1A
Figure 1B
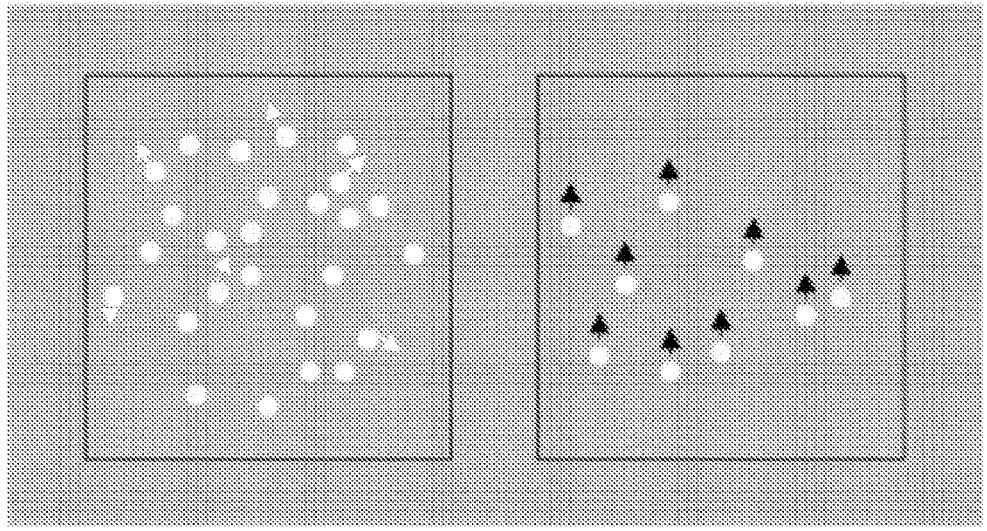

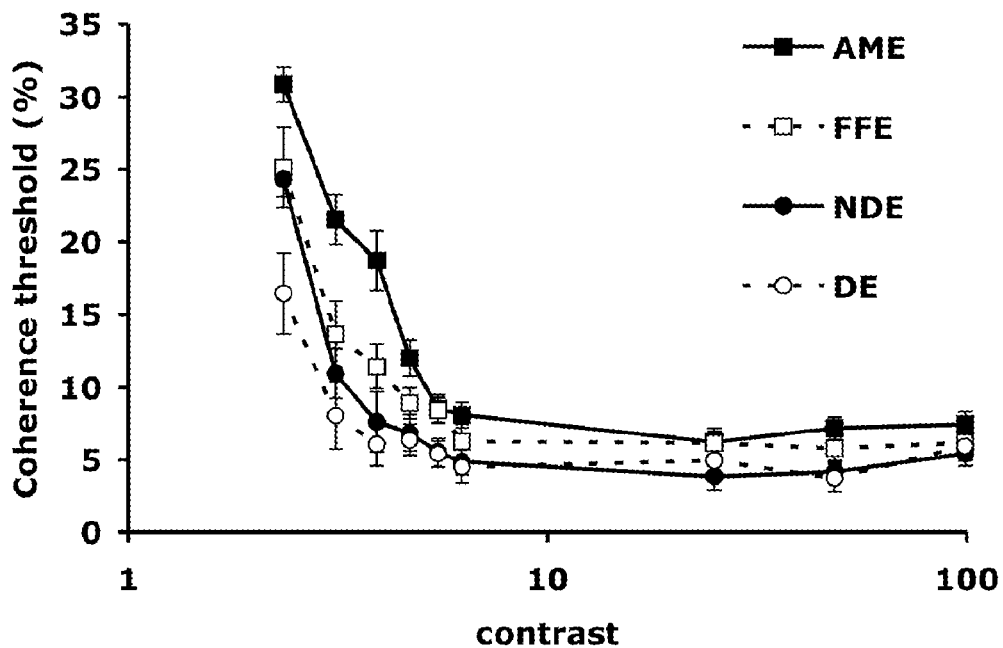
Figure 2A
Figure 2B
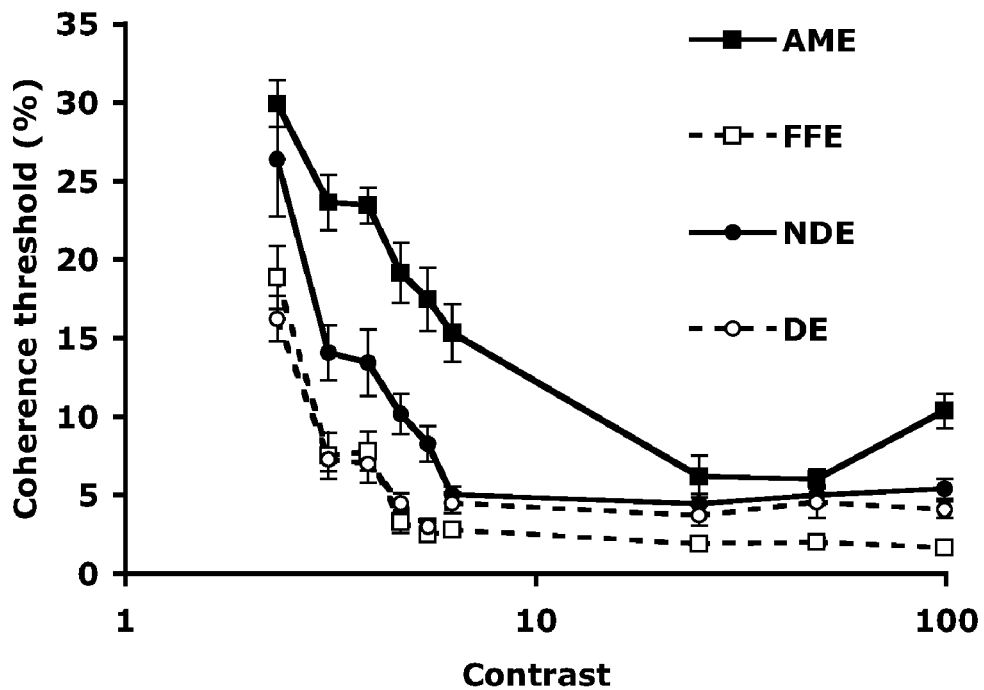

ED

GN

ML

ML

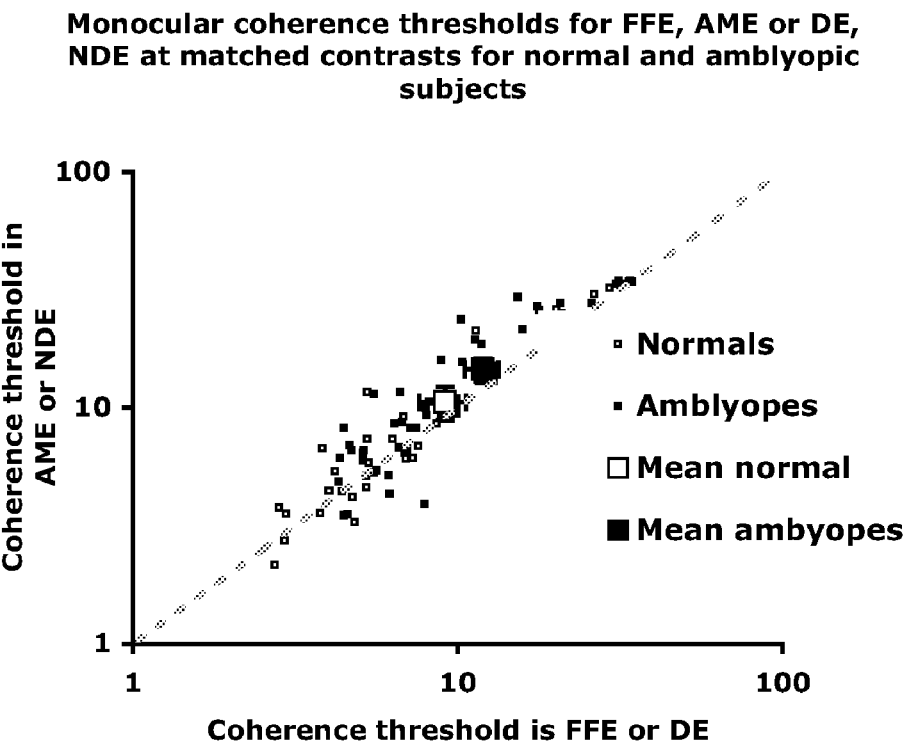
Figure 5A
Figure 5B
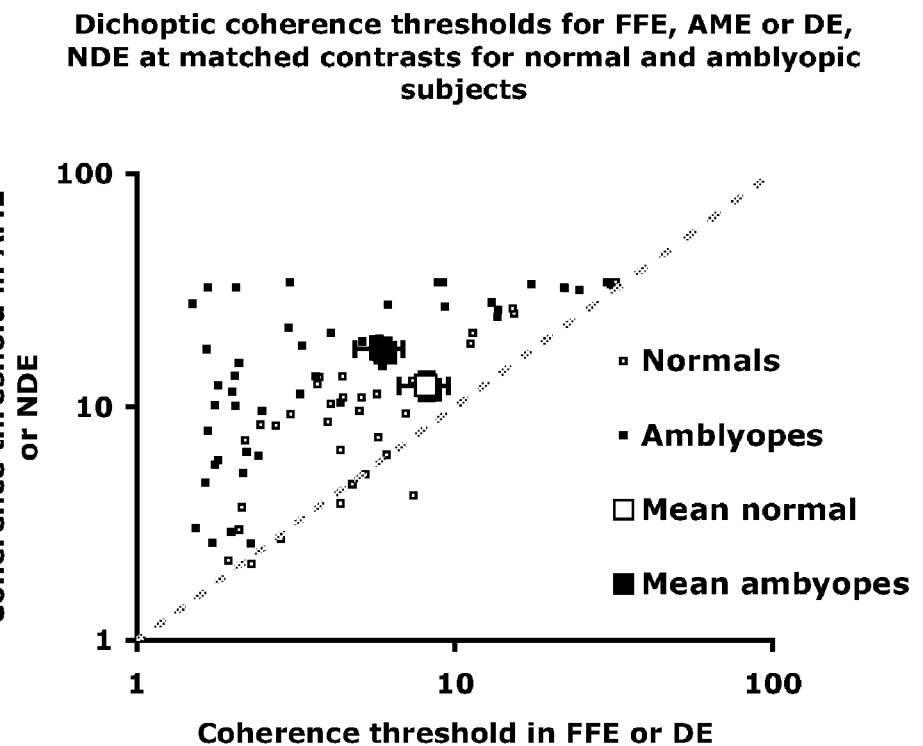

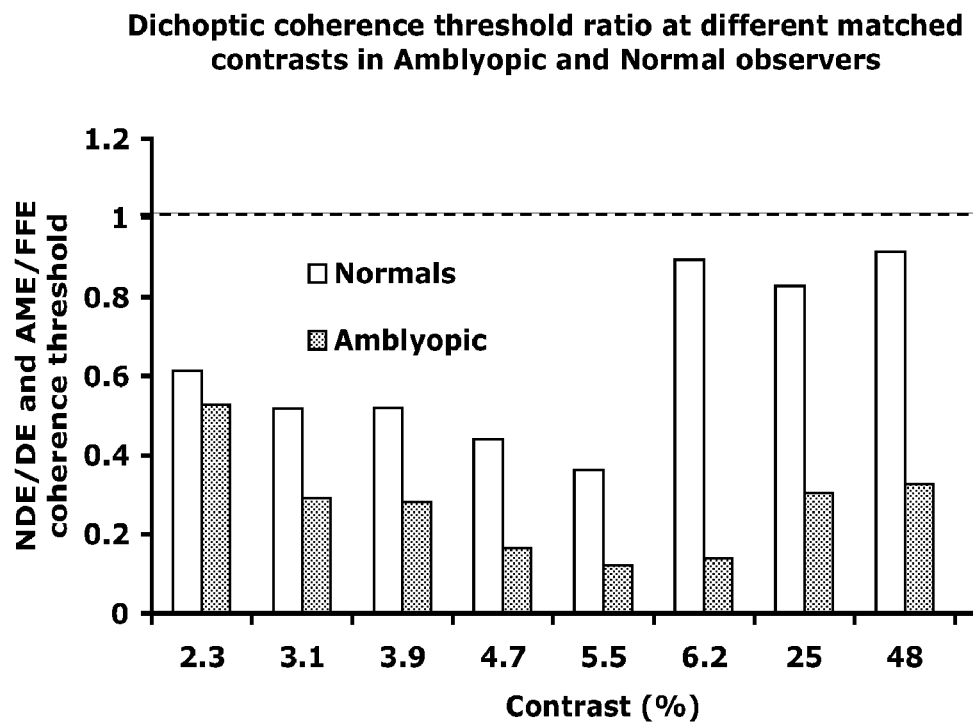
Figure 6
Figure 7A
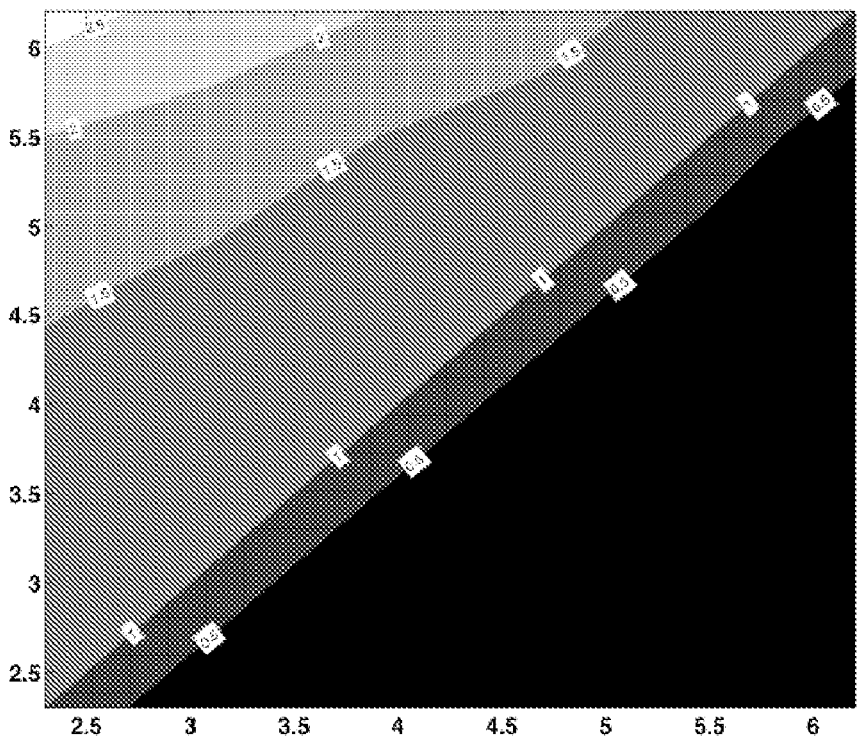

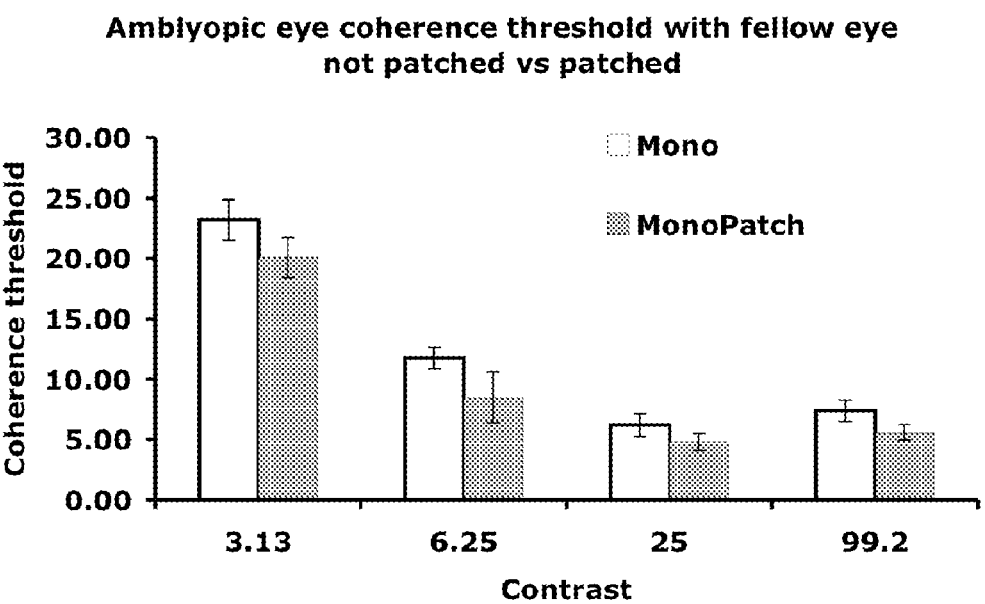
Figure 8
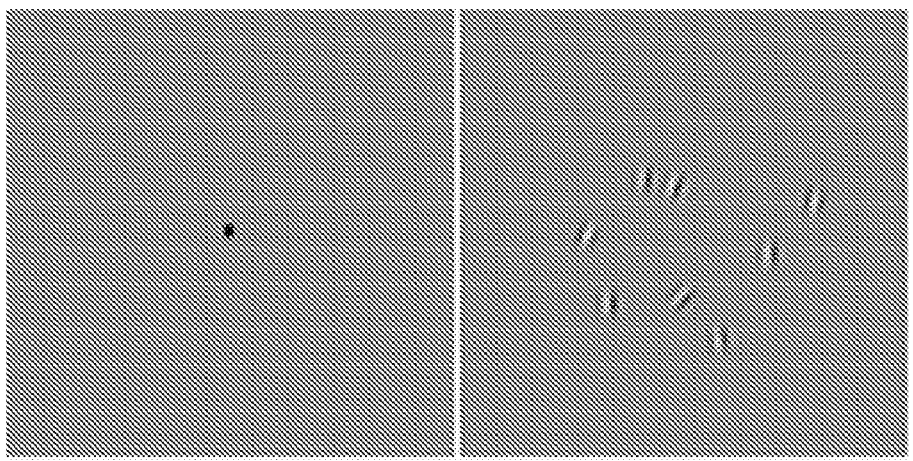
Figure 9A
Figure 9B
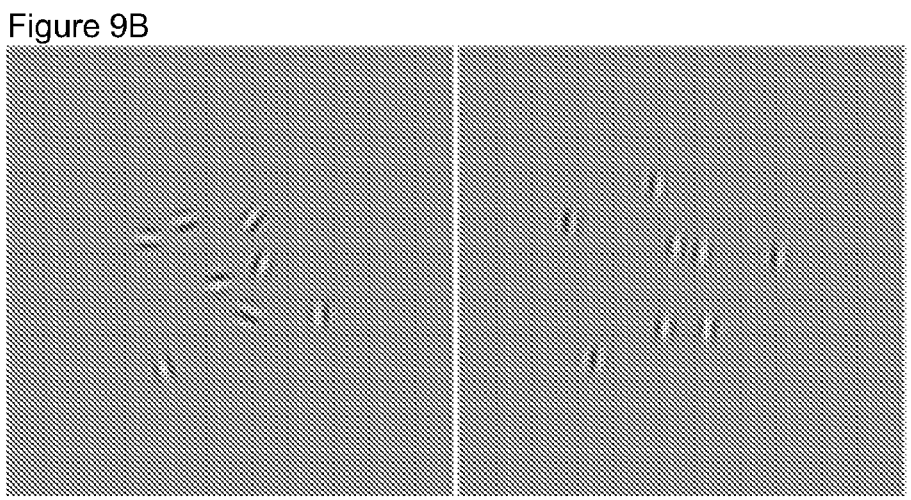

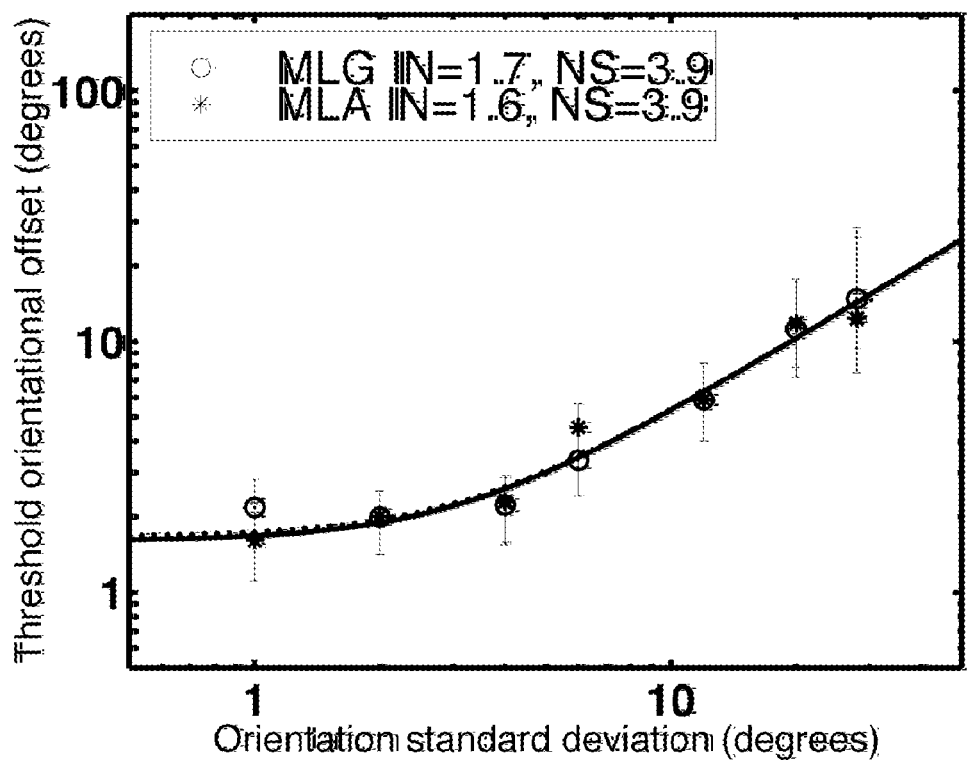
Figure 10
Figure 11A
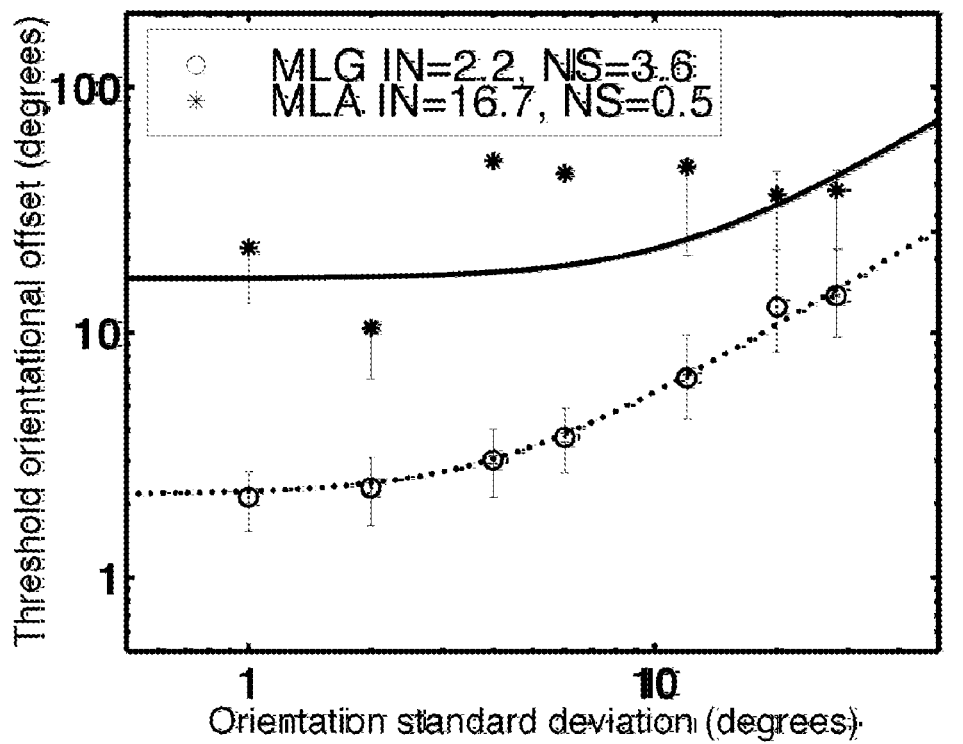

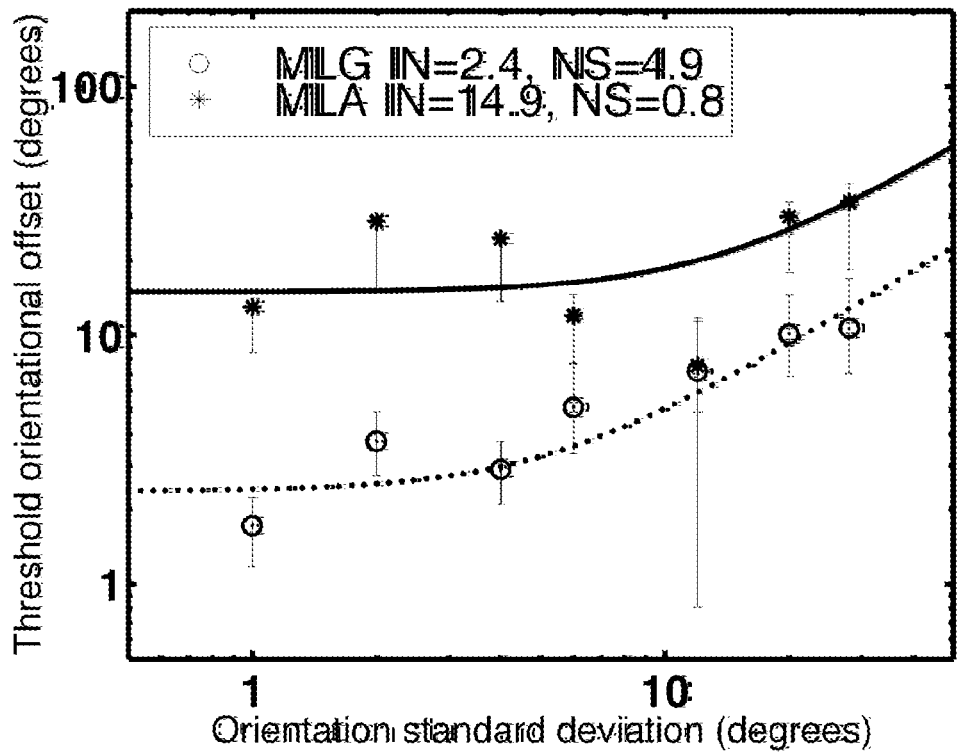
Figure 11B
Figure 11C
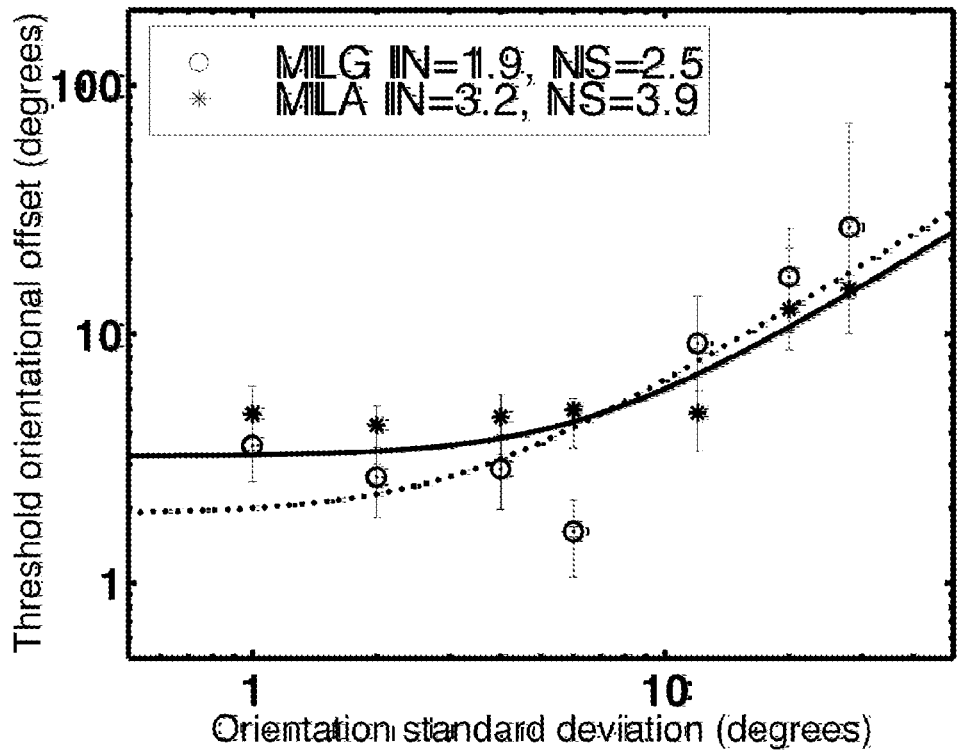

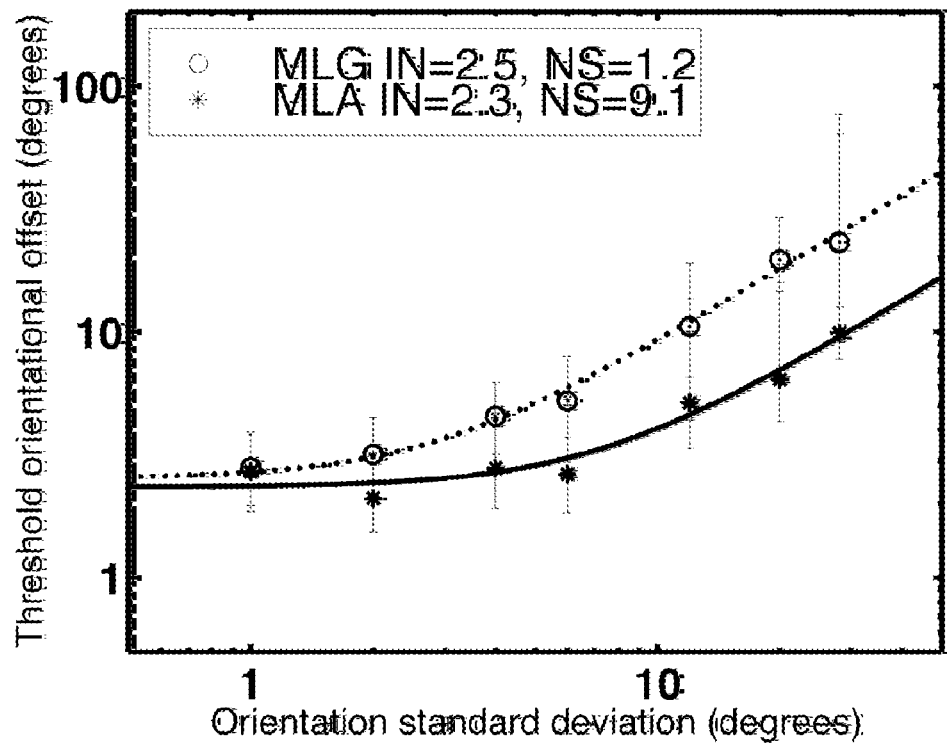
Figure 11D
Figure 12A
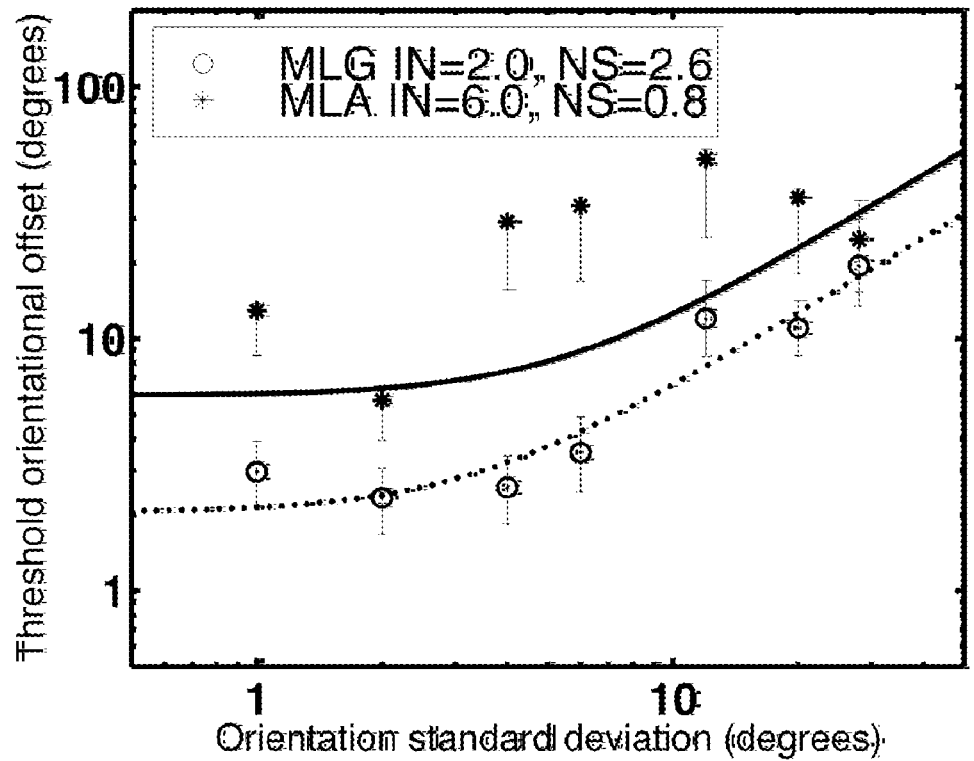

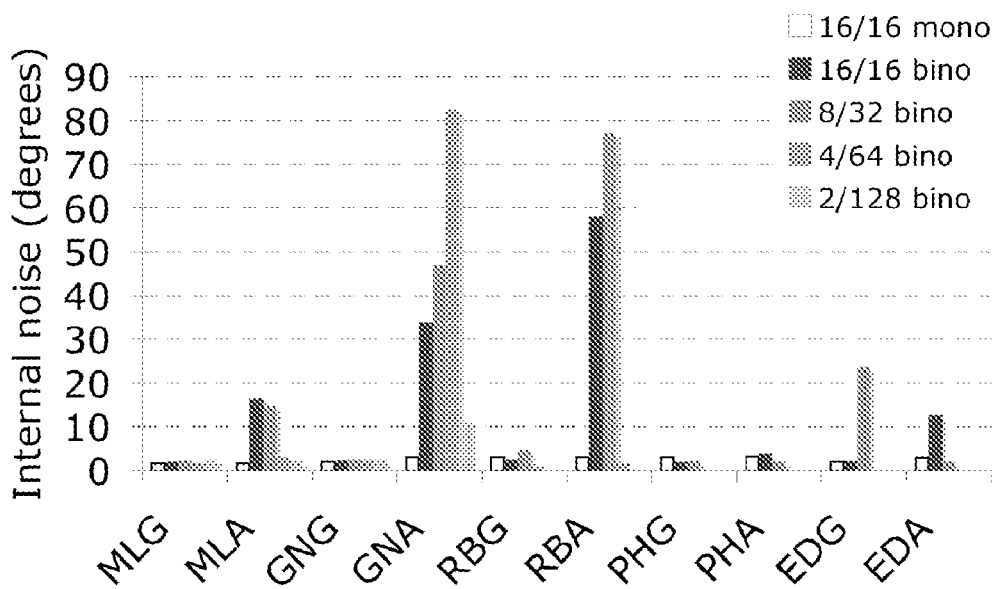
Figure 13A
Figure 13B
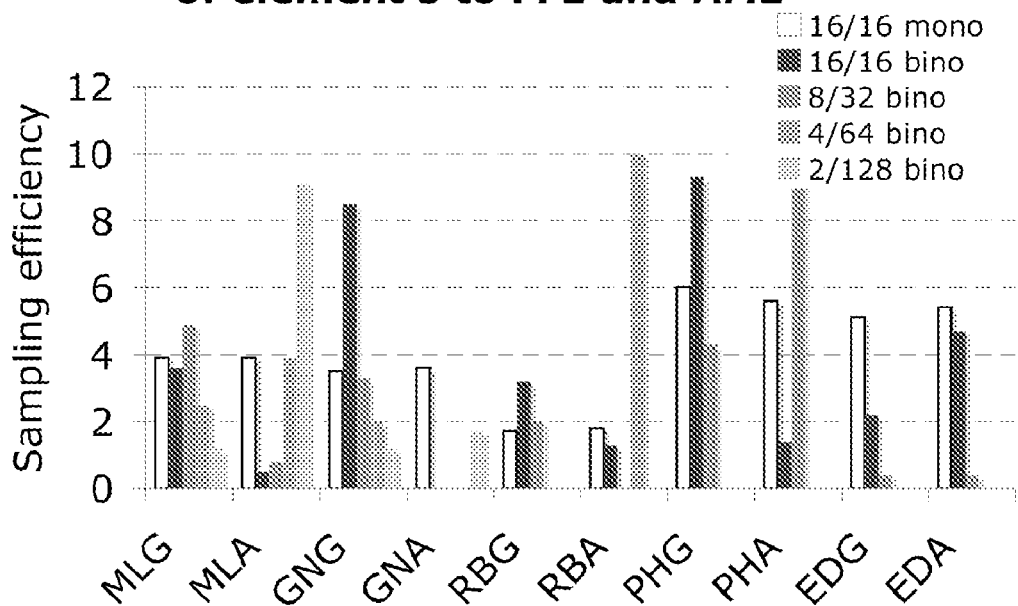

A

B

BINOCULAR VISION ASSESSMENT AND/OR THERAPY

The present application is a Continuation-in-Part of now pending U.S. application Ser. No. 12/528,934, filed Mar. 15, 2010, which claims priority to U.S. Provisional Application 60/981,859 filed Oct. 23, 2007 and to U.S. Provisional Application No. 60/987,078 filed Nov. 11, 2007 the specifications of which are hereby incorporated by reference.

TECHNICAL FIELD

The present invention relates to a method and to an apparatus for assessing and/or treating deficiencies in binocular vision.

BACKGROUND

Loss of binocular function is a common symptom of numerous visual disorders, which result in a loss of depth perception. Although there are many diverse causes of poor binocular function, the most extreme one is a condition called amblyopia, the world's most common cause of monocular blindness in adults. The health systems of many countries have, at great expense, developed screening programs to detect amblyopia in children, however when discovered, there is little that can be done to treat the problem. The amblyopic eye (AME) is subject to suppression from the fellow fixing eyes (FFE) whereby under binocular viewing conditions, information from that eye is not used. Treatments such as patching or penalizing the FFE have concentrated on improving monocular function of the amblyopic eye.

Standard of care for amblyopia, in addition to patching, requires regular visits to an eye care specialist such as an ophthalmologist or an optometrist for routine evaluation of treatment efficacy and disease regression/progression. A typical patching regimen has important drawbacks because it does not allow the fellow eye (good eye) to contribute normally to binocular vision and can be troublesome for a youngster. It is therefore highly desirable to provide an apparatus and method that is enjoyable and avoids the above drawbacks.

SUMMARY OF THE INVENTION

Applicants' approach is unique in that it first sets out to reduce the suppressive influences exerted by the fellow eye on the amblyopic eye under normal binocular viewing conditions so that the two eyes can work together. Applicants feel that the important first step in the treatment of amblyopia is the restoration of binocular function. Applicants' invention has been designed around the need to improve binocular function, as a first step, in treating amblyopia by first addressing the suppressive interactions between the eyes but it is applicable to any condition where the symptom is poor binocular function, for example in the case of a turned eye or strabismus without amblyopia.

Applicants have discovered a way of activating the AME (or any weak eye) under binocular viewing conditions, a technique that could be highly beneficial for the treatment of amblyopia and other conditions in which a strong eye and a weak eye fail to work together properly, generally with impairment of binocular vision.

Applicants have also discovered a way of assessing a state of binocular vision health.

Applicants' invention concerns the measurement and treatment of monocular sensory visual loss associated with an unequal refractive error or a strabismus. Unlike previous inventions that are intended to passively aid the reduced vision of visually impaired patients (be they monocularly or binocularly impaired) by electronically enhancing images (U.S. Pat. No. 6,912,301 B1), Applicants' invention involves the measurement and active treatment of the suppressive influences that operate in patients with only one eye visually impaired. Prior art has addressed the measurement (EP 1 082 939 A2) and treatment (EP 0 830 839 A2; U.S. Pat. No. 5,936,126) of the muscular dysfunction underlying a strabismus. Applicants' invention does not address the muscular dysfunction but rather the sensory loss that is a separate entity and can occur in the absence of a strabismus. Prior art dealing with the sensory loss has used one of two approaches. In the first approach, the vision of the fellow good eye is occluded either physically or electronically (U.S. Pat. No. 6,511,175 B2; U.S. Pat. No. 5,264,877; U.S. Pat. No. 4,726,672; U.S. Pat. No. 5,452,026) with the goal of forcing the amblyopic eye to work. Applicants' invention does not involve the use of occlusion. The second approach involves binocular viewing of a scene where some extended image contours are seen exclusively by one eye and other extended contours, by the other (US 2006/0087618A1). In other words the images seen by either eye are spatially and/or temporally distinct, being different components of a composite image (eg clockface vs clock hands). This approach does not lend itself to a quantitative and valid measurement of the degree to which the different monocular images are combined binocularly and therefore cannot in itself guide treatment.

Applicants' invention does not utilize this approach. Although the apparatus separately displays right eye and left eye information (i.e. dichoptic display) this information must have comparable spatial or temporal (e.g. motion) properties calculated over the image as a whole. Furthermore, applicants adjust the strengths of the relative right eye/left eye information content to obtain a quantitative and valid measurement of the degree to which the different monocular images are combined binocularly. Applicants use a signal/noise approach where the information seen by one eye contains signal to accomplish the task at hand, whereas the information seen by the other eye contains noise designed to disrupt performance (i.e. signal/noise paradigm). The extent to which the noise seen by one eye disrupts performance gives a direct performance-related measure of how well information seen through that eye is combined with information seen by the other eye.

By information content applicants mean the overall luminance, local contrast, motion direction, motion speed, spatial sampling, spatial frequency and orientation of local image features. While the present approach uses a signal/noise paradigm it could be generalized to other stimuli where the information content of left and right images are systematically varied in a way that lends itself to a quantitative measure of the extent to which information from the two eyes are combined binocularly. Applicants model the combination of signal and noise in an analysis of the derived threshold performance and systematically adjust the balance of the information seen by each eye to obtain optimal binocular performance thresholds for the task. This gives a balance of information that a particular visual system can tolerate and a benchmark from which to gauge treatment progress. It supplies a scientifically valid measurement of the degree to which a stronger eye suppresses a weaker eye in cases of anomalous binocular vision. As a result of repeated measurements, the balance point gradually changes towards 50:50, which is the balance point in a normal individual with good binocular vision. Applicants use two different tasks based on the above principle to specifically target the functioning of the two major pathways carrying visual information in the extrastriate cortex, the ventral and dorsal pathways. Applicants use global spatial tasks to target the former and global motion tasks to target the latter.

Instead of patching a strong eye to exercise the weak eye, Applicants have discovered that the presentation of different images to both eyes can stimulate binocular vision. The different images may contain different information content, with the strong eye receiving less information than the weak eye.

The information content difference between the images presented at which a patient begins to experience binocular vision is an indication of the degree of binocular vision health. The treatment begins with an initial measurement of the degree to which the information content of the left and right images needs to be imbalanced for binocular combination to take place. This is called the balance point and represents a scientifically valid measure of the degree of interocular suppression. A training regime of duration between 1-2 hours is commenced such that images are presented with informational imbalances at and near to the previously measured balance point and psychophysical performance is monitored at these balance points for the task, be it motion direction discrimination or orientational discrimination. At the end of this training session, the balance point is re-measured using the same stimuli and tasks. If the balance point reading remains stable for 3 such treatment sessions, further treatment is discontinued. If the balance point reading reduces, further treatment is planned and this assessment/treatment cycle continues until the balance point value reaches an asymptotic value, signified by three consecutive balance values that are statistically indistinguishable. The assessment of the balance point is made by a clinically trained eye-care professional whereas the treatment may be implemented in a portable take home device whose performance related measures will be stored and able to be accessed subsequently by the eye care practitioner.

A variable difference between a left eye image and a right eye image is adjustable to achieve binocular vision in a patient having a deficiency of binocular vision. A source of image pairs is used along with a dichoptic display system to present a selected one of the images pairs as a right eye image to a patient's right eye and a left eye image to a patient's left eye. The variable difference at which a patient achieves binocular vision is a measure of a level binocular vision health or function, and continued exposure to the image pairs is therapeutic. The variable difference can be adjusted during therapy and restoration of regular binocular vision is possible.

Information content can take a variety of forms. Contrast, overall luminance, sampling, resolution, filtering, temporal, motion, orientation and contour are all examples of image characteristics that affect information content as perceived by the human brain. Some of these image characteristics can only be altered by image processing, while others may be altered by physical filters. Processed images having the desired information content difference can be recorded or stored for later display, or computer generated as required. Binocular vision can be experienced in patients having loss of or diminished binocular vision due to a strong eye/weak eye imbalance using images having information content difference with respect to one or more of these image characteristics. Preliminary results show that the amount of difference at which binocular vision is experienced can be different for different image characteristics.

The information content difference is selected or adjusted until a patient or user experiences binocular vision. This stage is useful for assessment of binocular vision health, and when continued, restores aided binocular vision and exercises the weak eye while forcing both eyes to work together. To improve binocular vision and work toward restoring unaided binocular vision, the information content difference is reduced, typically very gradually, with the goal of improving the ability for both eyes to work together.

It is an object of the present invention to provide a binocular vision assessment and/or therapy apparatus comprising a source of left eye image and right eye image pairs adapted to be viewed dichoptically and perceived with binocular vision, the pairs having a variable difference between the left eye image and the right eye image; a dichoptic display system presenting a selected one of the images pairs as a right eye image to a patient's right eye and a left eye image to a patient's left eye; and a proper use detector having a camera for imaging a patient using the dichoptic display system and an image analyzer for determining proper use of the display system by the patient.

It is another object of the present invention to provide a binocular vision assessment and/or therapy apparatus comprising a handheld computing device having game software defining a task to be performed by a patient by interaction with the device, the software including a source of left eye image and right eye image pairs adapted to be viewed dichoptically and perceived with binocular vision, the pairs having a variable difference between the left eye image and the right eye image; and the computing device being adapted to present a selected one of the images pairs as a right eye image to a patient's right eye and a left eye image to a patient's left eye, wherein the software records patient task performance and synchronizes task performance data collected over time with a data network for access by a health care professional.

It is yet another object of the present invention to provide a binocular vision assessment and/or therapy apparatus comprising a handheld computing device having a stereoscopic lenticular screen overlay for stereoscopic viewing without stereoscopic glasses and game software defining a task to be performed by a patient by interaction with the device, the software including a source of left eye image and right eye image pairs adapted to be viewed dichoptically and perceived with binocular vision, the pairs having a variable difference between the left eye image and the right eye image; and the computing device being adapted to present a selected one of the images pairs as a right eye image to a patient's right eye and a left eye image to a patient's left eye.

One aspect of the present invention is a treatment and/or assessment based on a modified version of the video game Tetris, which is one of the most popular, commercially successful and enjoyable video games available today. During play, active game elements (i.e. blocks) are rendered separately to two eyes, sending maximum contrast to the amblyopic eye, to encourage it to work alongside with the fellow eye, which receives lower supra-threshold contrast. When game performance becomes stable at a given contrast ratio, game difficulty is adjusted by raising the contrast for the fellow eye. Applicants have developed a device for take-home use that can be used to improve binocular vision by reducing suppression with the side effect of also reducing amblyopia.

This invention is a game platform for the assessment and/or treatment of disorders of binocular vision, such as amblyopia. The game content is devised to maximize the possible therapeutic effects by leveraging advanced research in ophthalmology, as well as advanced display technology to render images independently to each eye. In particular, the game content engages both eyes at different levels of difficulty, forcing an amblyopic eye to work harder to regain its performance in the visual system. The invention herein described provides a mobile device, capable of interaction with an eye care specialist, for the assessment/treatment of binocular vision using innovative mechanisms for ensuring proper use thereof.

BRIEF DESCRIPTION OF THE DRAWINGS

The invention will be better understood by way of the following detailed description of a preferred embodiment, with reference to the appended drawings, in which:

FIG. 1: Schematic presentation of the random dot kinematogram is shown for monocular (A) and binocular (B) conditions. Black arrows show the signal dots, which were moving, in the same direction (up vs down) within a trial. White arrows represent the noise dots, which were moving in random directions. In the monocular condition, signal and noise dots were presented to one eye at a time (A). In the binocular condition, signal and noise dots were presented to different eyes within each trial.

FIG. 2: Average contrast sensitivity threshold data for motion direction (exp. 1) for 7 amblyopic and 8 normal subjects is shown for amblyopic subjects' AME (solid line and filled squares) and FFEs (dashed line and open squares) and for normal subjects' non-dominant (solid line and filled circles) and dominant (dashed line and open circles) eyes for monocular (A) and binocular (B) conditions. The Y-axis represents the coherence threshold (%) in linear scale. The X-axis represents the contrast in logarithmic scale.

FIG. 5: Individual data points and average data for the coherence thresholds of the amblyopic and non-dominant eyes (filled squares) versus the fellow fixing and dominant eyes (open squares) are presented for monocular (A) and binocular conditions (B). The X-axis represents the coherence thresholds for the FFE and DE and the Y-axis represents the corresponding data for the AME and NDE. The dotted line shows the ratio of one line where the thresholds in two eyes would be the same.

FIG. 6: Average coherence threshold ratios for the non-dominant and dominant eyes in 8 normal observers and amblyopic and FFEs in 7 amblyopic subjects are presented at different stimulus contrasts. The X-axis represents the contrast (%) and the Y-axis represents the coherence threshold ratio for the amblyopic subjects (AME/FFE) (closed bars) and normals (NDE/DE) (open bars).

FIG. 8: A comparison of the performance of the AMEs under monocular conditions with patching of the FFE (closed bars) and without patching of the FFE, which saw mean luminance, instead (open bars) is presented. The X-axis is the percent contrast and the Y-axis is the coherence threshold (%). Error bars represent +/−1 SD.

FIG. 9: Schematic dichoptic mean orientation is presented for monocular (A) and binocular (B) conditions. In (A) only signal elements are presented to one eye and mean luminance plus fixation point to the other. In (B), signal elements are presented to one eye (right image in this presentation) and noise elements to the other eye (right image in this presentation).

FIG. 10: Mean orientation discrimination thresholds are presented for FFE (circles and dashed line) and AME (stars and solid line) for one amlyopic subject (ML). X-axis represents orientation standard deviation (°). Y-axis represents threshold orientation offset (°). Internal noise (IN) and sampling efficiency (NS) parameters which were derived from fitting the equivalent noise model to the data are presented in the inset. The contrast of the stimuli to FFE is 50% and to AME is 75%. At this combination of contrasts, the two eyes of this subject showed similar local orientation discrimination thresholds.

FIG. 11: Mean orientation discrimination thresholds are presented for FFE (circles and dotted lines) and AME (stars and solid lines) for AME/FFE number of elements ratio of 16/16, 32/8, 64/4, and 128/2 for A-D, respectively. Internal noise (IN) and sampling efficiency (NS) parameters are presented in insets. The X-axes represent orientation standard deviations (°). Y-axes represent threshold orientation offset (°).

FIG. 13: The internal noise (A) and sampling efficiency (B) is presented in this graph for 5 amblyopic subjects. One monocular condition (16/16) (open bar) and 4 binocular conditions (16/16 to 2/128) (from black to light grey) are presented for AME (A) and FFE (G) of the subjects.

DETAILED DESCRIPTION

Applicants applied techniques widely used in the study of higher level visual processing to the question of binocular vision in amblyopia. Specifically applicants used a classic signal/noise paradigm which applicants applied dichoptically, whereby signal was presented to one eye and noise to the other to assess binocular interactions in amblyopic observers. The rational was that if the eye receiving the signal was unable to process the information with which it was presented due to suppression, then only the noise presented to the other eye would be visible and the task associated with the signal population would be impossible. However if some information was available through the eye seeing the signal population, a behavioral measure of task performance would allow the applicants to quantify exactly how much information this eye was providing. Importantly, as the two populations of signal and noise were distinct, applicants were able to independently manipulate certain attributes of either population such as the contrast or the number of samples present in the population. In this way applicants were able to independently adjust the stimuli presented to each eye and to measure the contribution from each eye to binocular performance. Applicants found that under certain conditions where a reduced amount of stimulation was presented to the FFE and an enhanced amount to the AME, applicants could 'balance' the two eyes and measure behavioral responses clearly indicative of existing but weak binocular function in their amblyopic subjects. This was true for stimuli independently targeting either the dorsal visual processing stream (motion processing, experiment 1) or the ventral processing stream (form processing, experiment 2). Applicants were also able to precisely quantify the interactions between the two eyes by measuring the ratio of the difference between the two stimulus populations, e.g. the ratio of the contrast presented to the fellow eye vs. that presented to the AME.

Before describing the details of specific experiments, an overview of the basic apparatus according to two embodiments of the invention will be described with reference to FIGS. 15a and 15b, and the assessment and therapy using one embodiment of the invention will now be described with reference to FIG. 16.

Figure 15A:
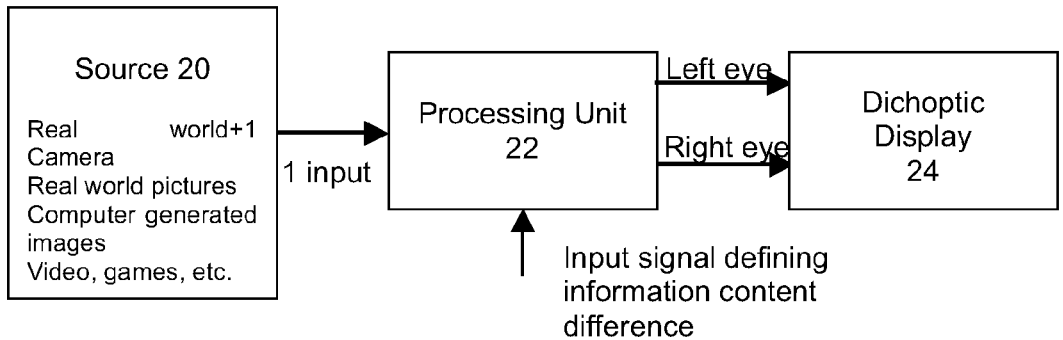
FIG. 15a is a schematic block diagram of a first embodiment of the invention in which a dichoptic monoscopic display is used.
Figure 16:
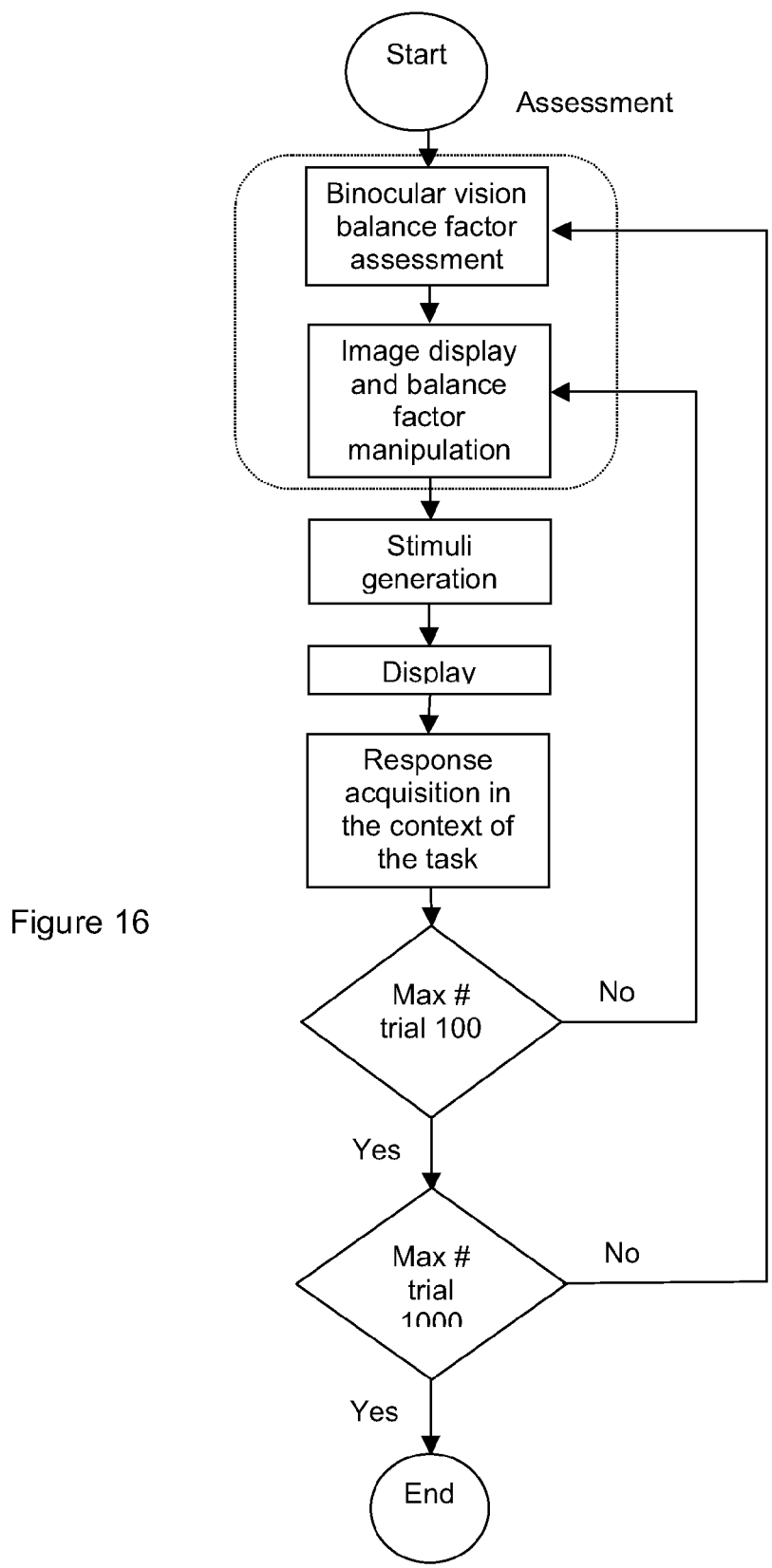
FIG. 16 is a flow chart of steps involved in a method of treating an amblyopic patient in one embodiment of the invention.

In the embodiment of FIG. 15a, an image source 20 comprises a camera or a computer image generator. The desired image is then processed by processor 22 in response to an input variable information content difference or ratio signal. In the case of a camera image, image filtering techniques (i.e. software) may be used to alter the information content, while in a computer generated image, selected image components may be selectively included or not in the different images. A dichoptic display system 24 is used by a user to view the images. A dichoptic display system is essentially a stereoscopic display system in which the displayed images are not different perspective images resulting in a 3D effect. Such display systems are well known in the art. It will be apparent to a person skilled in the art how to program a general purpose computer to provide a suitable user interface to control the adjustment of information content difference between right eye and left eye images displayed by the dichoptic display system.

Figure 15B:
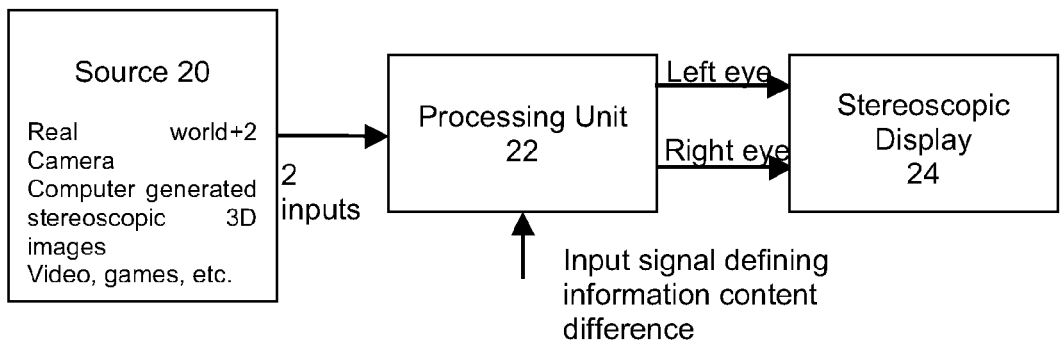
FIG. 15b is a schematic block diagram of a second embodiment of the invention in which a stereoscopic display is used.
Figure 15C:
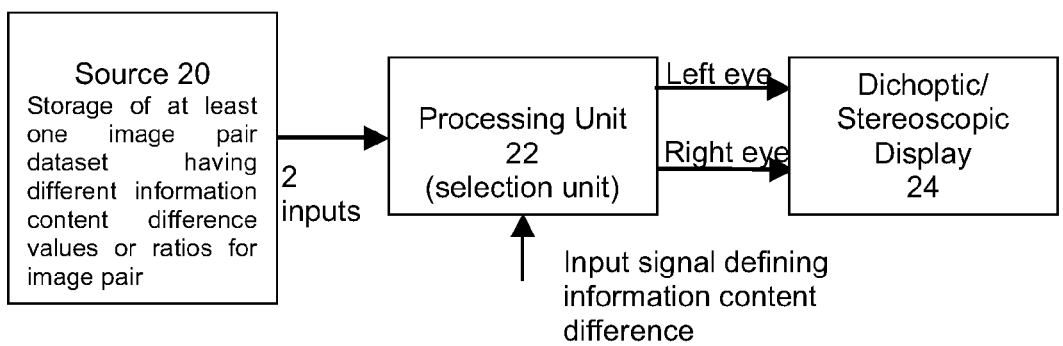
FIG. 15c is a schematic block diagram of a third embodiment of the invention in which the variable amount of information content difference is selected by selecting an appropriate image pair from a store of image pairs.

In the embodiment of FIG. 15b, the apparatus provides stereoscopic images, and thus the image source 20 is a stereoscopic image pair, and the image processor 22 alters the information content between the images, while respecting the different perspective information provided by the image pair. In the embodiment of FIG. 15c, the image source 20 is a store of at least one set of image pairs having a range of information content differences. As can be appreciated, the image store may contain tens, if not hundreds, of image pairs within a set, particularly when the information content difference is to be selected as a function of different image characteristics. In this embodiment, the image processor 22 is more of an image selection device that selects the appropriate image pair in response to the input desired difference signal. The image pair selected may be stereoscopic or not.

The apparatus of FIGS. 15a to 15c may comprise a general-purpose computer having suitable memory and data storage capabilities. The processor 22 may comprise suitable software executed by the computer, and the image source 20 may comprise the computer's data storage, a camera interface, a computer image generator program executed by the computer, or a suitable alternative, as will be appreciated by those skilled in the art. The video graphics electronics and software and display devices, including any shutter glasses, polarized lens glasses or prism glasses, that make up display 24 may involve components of a computer used for elements 20 and 22. A computer may also be programmed to provide a user interface for providing a user or operator with the ability to select the information content difference signal and other parameters, and additionally the interface may record user responses for analysis. The apparatus may also include a video game console or a personal computer equipped with video game software designed to allow for binocular separation of the visual information within the game either evenly or unevenly between the eyes. The display device may also incorporate technology to allow for an immersive virtual reality environment.

Therapy involves sessions of repeated image presentation, response acquisition and image modification. At the beginning, the binocular vision "balance factor" is assessed for each image attribute, using a task where the information from each eye is required. On the basis of the obtained "balance factor", image information content is modified, for example, images with reduced content information are presented to fellow eyes and images with augmented information content to the amblyopic eye, and responses are acquired in the context of the task. Feedback in the form of the task performance determines whether further modification of image content is necessary. After a number of repetitions binocular vision and stereovision are assessed. The aim is, through repeated trials, to affect a permanent change in the original balance factor in such a way that comparable information can be shown to each eye and used to obtain better performance on the dichoptic task. The training may also take the form of a video game either specifically designed for this purpose or modified by the image processing/display apparatus to facilitate training.

In an alternative embodiment, the apparatus comprises a user interface device in the form of a dial allowing the user to manually set the level of information content difference required in each eye for binocular vision. It is important for assessment and treatment of binocular vision deficiencies to perform all experiments above the threshold at which binocular vision is achieved. The dial allows continuous or step wise adjustments of information content such as overall luminance, local contrast, motion direction, motion speed, spatial sampling, spatial frequency and orientation of local image features. Another user interface device in an alternative embodiment can comprise computer screen user input objects, buttons, or stick (joystick) which allow the user to select an input during a task. For example in a motion determination task, the user selects one button when upward motion is perceived or another button when downward motion is perceived. In an orientation task, the user can select the orientation of gabors on a joystick, a dial or a series of buttons. Performance obtained by a user during any such task can be recorded by the apparatus, the data can be analyzed by software on a computer and plotted to allow easy interpretation and evaluation of therapeutic success of the regimen.

Use of a computer and software to capture data, analyze data and present pertinent data to the eye specialist is a further aspect of the invention since the measurement information content to each eye which is performed before each series of tasks as well as the actual results of the previous task allows the eye specialist (or the computer and software) to follow the success of the treatment regimen and to adjust treatment protocol, frequency and duration accordingly.

For a user with binocular vision deficiencies such as amblyopia, the information content presented to the weak eye is greater than that presented to the strong eye for binocular vision to be achieved and therefore the calculated balance factor, which is simply of ratio of information content of the weak eye over the information content to the strong eye, will be greater than 1. Therapeutic efficiency is reached when the balance factor approaches, or ideally reaches 1 (50:50 contribution of each eye to binocular vision). Treatments which consist of repeated tasks are stopped either when the balance factor reaches 1 or when several consecutive tasks do not lead to an improvement in binocular vision (i.e. a decrease in the balance factor).

In an alternative embodiment, the computer and software can use real world images and selectively blur information rich areas of the strong eye image in order to favor information content processing from the weak eye, thus contributing to the improvement of binocular vision.

In yet another embodiment, the apparatus can include specialized glasses that can be worn such as LCD glasses or shutter glasses. These glasses can be connected, wirelessly or not, to a computer which contains the software necessary to coordinate and run the binocular vision treatment regimen.

Experiment 1—Dorsal Pathway Binocular Interactions

The dorsal visual processing stream is thought to deal predominantly with motion information (Wurtz & Kandel, 2004). Accordingly, to study the dorsal pathway, applicants used random dot kinematograms (RDKs) to assess the binocular function of this pathway in amblyopia. Applicants used a coherence motion task. These stimuli are typically constructed of two populations of moving dots. The 'signal' population all move in the same direction termed the 'coherent' direction. Conversely, the 'noise' population has no common motion direction as all the dots move in random directions. The ratio of signal to noise dots required to recover the coherent motion direction is called the motion coherence threshold. The measurement of motion coherence thresholds is a well studied paradigm with regard to global motion integration (Braddick, 1974; Newsome, Britten, Salzman & Movshon, 1990; Newsome & Pare, 1988). One additional benefit of this paradigm is that it also provides a measure of signal noise segregation.

Motion coherence stimuli provide two sources of signal and noise whereby integrating the former increases performance and integrating the latter disrupts performance. Therefore, by using these stimuli with signal and noise separated dichoptically, one can independently study the mechanisms responsible for combining information from two eyes and measure the contribution of each eye to overall visual perception.

Applicants reasoned that if signal dots were presented to the amblyopic eye (AME) and noise to the fellow fixing eye (FFE), then the ability to perceive the coherent motion direction would only be possible if the AME were able to overcome the suppression of the FFE. In addition applicants could ensure that the two eyes were functioning binocularly by measuring motion coherence thresholds, a measurement that is only possible if both signal and noise populations are contributing to the final percept.

Applicants found that under dichoptic presentation of the signal and noise with similar contrast, the coherence threshold was higher when signal dots were presented to the AMEs and noise dots to the fellow eyes comparing to when signal dots were presented to the FFEs and noise to the AME. The higher coherence threshold in the former condition suggests that less information from the AME is contributing to visual perception. However, increasing the number of signal dots presented to the AME, as part of coherence threshold measurement, the binocular visual system started to fuse the images from two eyes and so could perform the task. This finding suggests that presenting proportionally more signal dots to AME can compensate for its visual deficiency.

Applicants also manipulated the contrast of the stimuli presented to each eye independently where applicants presented the stimuli to FFEs at lower contrasts than those presented to the AMEs. Applicants found that with a certain ratio of contrasts between the two eyes (less contrast to the FFE) the AME was able to participate in the task and binocular vision was achieved, which indicates that presenting stimuli with higher contrasts to the AME can also compensate for its deficiency. The exact contrast ratio varied on an observer to observer basis. Importantly however, it was not the same as the difference in monocular contrast thresholds for this task, whereby both signal and noise populations were presented to one eye at a time. This demonstrated that dichoptic presentation yielded a true measure of binocular interaction.

As a final control applicants also measured monocular coherence thresholds in the AME when the FFE was either patched or viewing mean luminance. This provided a measure of the level of suppression of the AME elicited just by having the FFE open.

Experiment 2—Ventral Pathway Binocular Interactions

In a separate but similar experiment, applicants applied the same idea of (a) signal/noise binocular integration and (b) manipulating the number of samples and contrast for dichoptically presented form (e.g. orientation) stimuli. Applicants used a global mean orientation discrimination task where a patch of oriented Gabors were presented to the observers and they were asked to make judgments about the mean orientation, specifically, whether it was tilted to the left or right of vertical (see Methods of (Mansouri, Allen, Hess, Dakin & Ehrt, 2004)). The orientations of the signal Gabors were randomly selected from a predetermined population with a specific mean and variance. The orientations of the noise Gabors were selected from a flat distribution. Similar to experiment 1, applicants reasoned that integrating signal Gabors improves performance whereas integrating noise Gabors disrupts the performance of the visual system. Applicants could objectively measure the contribution of either eye to visual perception, based on the eye to which signal or noise were presented.

to amblyopia should directly address the strengthening of this binocular system to overcome the suppressive mechanisms acting upon the AME.

Methods

Observers

Eight amblyopic and eight normal observers participated in the two experiments (seven and five amblyopic subjects completed experiment 1 and 2, consecutively). Refraction in all observers was tested and corrected to best visual acuity. The "Declaration of Helsinki" was followed and informed consent was obtained from all observers before data collection.

Eye dominance: Eye dominance for normal subjects was assessed for each subject using a sighting test (Rosenbach, 1903). Six subjects were right eye dominant, two were left eye dominant.

Apparatus (Exp. 1)

Stimuli were generated using Macintosh G4 and presented on a gamma-corrected Sony professional Series P22f monitor with a refresh rate of 75 Hz. The mean luminance of the display was approximately 50 cd/m$^2$. The RDKs were presented within a circular window at the centre of the display, which subtended 12° at the viewing distance of 92 cm.

TABLE 1

| Obs | Age/Sex | Type | Refraction | Dev | LA | Squint | History, stereo |
|---|---|---|---|---|---|---|---|
| AS | 21/F | RE | Ø | DS | 20/160 | ET 15° | Detected age 4 y, patching at 4 y for 6 m, |
|  |  | LE strab | −0.5 |  | 20/20 |  | surgery at 7 y, no stereopsis |
| AR | 47/M | RE | Ø |  | 20/20 | ET 1° | Detected age 6 y, no patching, no surgery |
|  |  | LE strab | Ø |  | 20/50 |  |  |
| ED | 43/F | RE | +0.5 | DS | 20/16 | ET 5° | Detected age 6 y, patching for 1 y, normal |
|  |  | LE strab | +0.5 | DS | 20/63 |  | local stereovision |
| GC | 20/F | RE | Ø |  | 20/20 | ET 1° | Detected age 7 y, patching for 1-2 y, No |
|  |  | LE strab | Ø |  | 20/50 |  | surgery |
| GN | 30/M | RE mixed | +5.00 − 2.00 | 120° | 20/70 | ET 8° | Detected age 5 y, patching for 3 m, no glasses |
|  |  | LE | +3.50 − 1.00 | 75° | 20/20 |  | tolerated, 2 strabismus surgery RE age 10- |
| JD | 21/M | RE strab | +4.00 | DS | 20/63 | ET 5° | Detected age 5 y, patching for 3 y, no surgery, |
|  |  | LE | +1.50 | DS | 20/16 |  | 2/10 local stereopsis |
| ML | 20/F | RE mixed | +1.0 − 0.75 | 90° | 20/80 | ET 6° | Detected age 5 y, patching for 2 y |
|  |  | LE | −3.25 | DS | 20/25 |  |  |
| PH | 33/M | RE | −2.0 + 0.5 | DS | 20/25 | ET 5° | Detected age 4 y, patching for 6 m, |
|  |  | LE strab | +0.50 | DS | 20/63 |  | Surgery age 5 y. |
| RB | 49/F | RE | +3.25 | DS | 20/15 | ET 10° | Detected age 6 y, glasses since 6 y, no other |
|  |  | LE strab | +4.75 − 0.75 | 45° | 20/40 |  | therapy, near normal local stereo vision |

Table 1 provides clinical details of the amblyopic observers participating in the experiment. The following abbreviations have been used; strab for strabismus, aniso for anisometrope, RE for right eye, LE for left eye, ET for esotropia, XT for exotropia, ortho for orthotropic alignment, sph for diopter sphere.

Applicants changed the contrasts under which applicants could obtain monocular matched performance for the AME and FFE of every individual subject as a baseline for this study. Applicants found that although both eyes could perform similarly when stimuli with matched contrasts were presented to each eye monocularly, when stimuli with similar contrasts were presented dichoptically, the AME could no longer contribute. Therefore the binocular system was inactive when presented with stimuli accounting for the monocular AME deficiency, were presented to two eyes. However, when weaker stimuli (i.e. less samples or less contrast) were presented to the FFE, the AME started to contribute to binocular vision.

The implication of these findings is that for both dorsal and ventral visual processing, binocular mechanisms in amblyopia, whilst weak, are intact. Therefore treatment approaches Stimuli (Exp. 1)

Global motion stimuli were translational random-dot kinematograms (RDKs). Dots were presented on a homogenous mid-grey background (mean luminance of 50 cd/m$^2$) that filled the entire circular display window. The luminance modulation (Michelson contrast) and hence the visibility of the dots could be varied by increasing the luminance of the dots, with respect to the background, according to the following equation:

Dot luminance modulation=$(L_{dots}-L_{background})/(L_{dots}+L_{background})$, where $L_{dots}$ and $L_{background}$ are the dot and background luminance, respectively. The luminance of the dots could be varied in the range 0.004 to 0.33. Each RDK was generated anew immediately prior to its presentation and was composed of a sequence of 8 frames, which when presented consecutively produced continuous apparent motion. The duration of each frame was 53.3 ms, resulting in a total stimulus duration of 426.7 ms. Each image contained 100 non-overlapping dots (dot density 0.88 dots/° 2) and the diameter of each dot was 0.235°. At the beginning of each motion sequence, the position of each dot was randomly assigned. On subsequent frames, each dot was shifted by 0.3°, resulting in a drift speed, if sustained, of 5.9°/s. When a dot reached the edge of the circular display window it was immediately re-plotted in a random spatial position within the confines of the window.

Procedure (Exp. 1)

The global motion coherence level of the stimulus was manipulated by constraining a fixed proportion of 'signal' dots on each image update to move coherently along a translational trajectory and the remaining ('noise' dots) to move in random directions. The signal dots direction could be either upwards or downwards on each trial with equal probability.

Experiment 1A, Monocular Condition

Both Eyes Open

Using a stereopscope the stimuli were randomly presented to one eye at a time within each run with all measurements carried out monocularly (see FIG. 1A). The observer was not aware of which eye was seeing the stimulus. Global motion thresholds were measured using a single-interval, forced-choice direction-discrimination procedure. On each trial, observers were presented with an RDK stimulus in which the signal dots moved along an upward or downward trajectory. The observers' task was to identify whether the motion was upwards or downwards. Data-collection was carried out using an adaptive staircase procedure (Edwards & Badcock, 1995). The staircase varied the proportion of signal dots present on each trial, according to the observer's recent response history. The staircase terminated after eight reversals and thresholds (79° A correct performance) were taken as the mean of the last six reversals. Each threshold reported was based on the mean of at least five staircases.

Fellow Fixing Eye Patched

In the previous condition, on every trial the stimuli were presented to one eye and background (i.e. mean luminance) to the other eye in a random order. The mean luminance to one eye did not carry any relative information to the purpose of the task, so it cannot theoretically contribute in the subjects' final decisions about the task (i.e. upward or downward motion). However, the light through the fellow eye could stimulate the retinal cells nonspecifically. In amblyopia where the balance of interaction between two eyes is disturbed, and any stimulation of the fellow eye can strongly grab the visual attention, mean luminance to the fellow eye might have had a detrimental effect on the AME performance due to suppression. In order to measure the effect of mean luminance to the fellow eyes when stimuli were presented to the AME, applicants also tested the subjects monocularly with the FFE occluded with a patch. The effect of mean luminance to the fellow eye on AME performance is especially interesting because most amblyopia studies use patching for monocular testing of the AME. If the difference between the mean luminance and no light conditions is significant, applicants should reevaluate the patching paradigm for monocular testing.

Experiment 1B, Dichoptic Presentation

In experiment 2 the RDKs were presented within two horizontally separated, circular display windows, each equidistant from the centre of the screen (see FIG. 1B). Images were viewed at a distance of 114 cm through a Wheatstone Stereoscope. Each circular window subtended 7° and to aid binocular fusion, each display region was surrounded by a rectangular frame.

Dots were presented on a homogenous mid-grey background. The luminance modulation (Michelson contrast) and hence the visibility of the dots could be varied independently in two eyes by increasing the luminance of the dots, with respect to the background in an identical manner to Experiment 1.

In Experiment 2, performance was measured for translational global motion under dichoptic viewing conditions. Each presentation contained two images (see FIG. 1). Previously, in the monocular viewing condition, the signal and noise were presented to one eye and a uniform grey field of mean luminance was presented to the other eye. In the dichoptic viewing condition, the signal was presented to one eye and the noise was presented to the other eye. Since applicants varied the contrast of the signal and noise independently, applicants were able to present stimuli with high contrast to the AME and low contrast to the FFE.

All measurements were carried out under dichoptic viewing conditions in an identical manner to that employed in experiment 1.

In all monocular and dichoptic viewing conditions, measurements were repeated with either the left eye or the right eye within the same run of trials. In this instance, performance was tracked and thresholds (79% correct performance) measured for each eye using a two interleaved adaptive staircase procedure. Each threshold reported is based on the mean of at least six staircases. For the monocular and dichoptic viewing conditions, the results for the left and right eyes were combined.

Results (Exp. 1)

FIG. 2 represents the average coherence threshold data for monocular (FIG. 1A) and binocular (FIG. 1B) conditions. In the monocular condition (A) amblyopic and FFEs showed higher thresholds than those of the normal eyes. However, at medium suprathreshold contrasts (e.g. 5-8%) the AMEs showed significantly higher than normal thresholds whereas the FFE threshold was close to those of the normal eyes. In the dichoptic condition (B) AMEs showed significantly higher thresholds at all contrasts tested. The normal eye average thresholds fall between those of the amblyopic and FFE at the higher contrasts suggesting that not only does the AME suffer from suppression from the FFE, but also that the FFE benefits from this phenomenon.

FIG. 3 shows the change in the ratio of the coherence thresholds in the fellow fixing and AMEs when they were independently presented with stimuli of different contrasts. Stimuli presented to the AMEs always had similar or higher contrasts compared to those presented to the FFEs. FIG. 3(A-D) represents data for 4 individual amblyopic subjects. When stimuli with the same contrast were presented dichoptically to both eyes, the thresholds were always higher in the AMEs meaning that when the stimulation to both eyes had the same energy, the AME was less efficient. However, increasing proportional contrast to the AME improved the performance of the AMEs to the extent that in most cases a sufficiently large contrast ratio provided motion coherence threshold ratios equal to 1 meaning that both eyes were performing equally. At higher proportional contrasts, the AMEs showed even better performance than the FFEs.

Figure 3A:
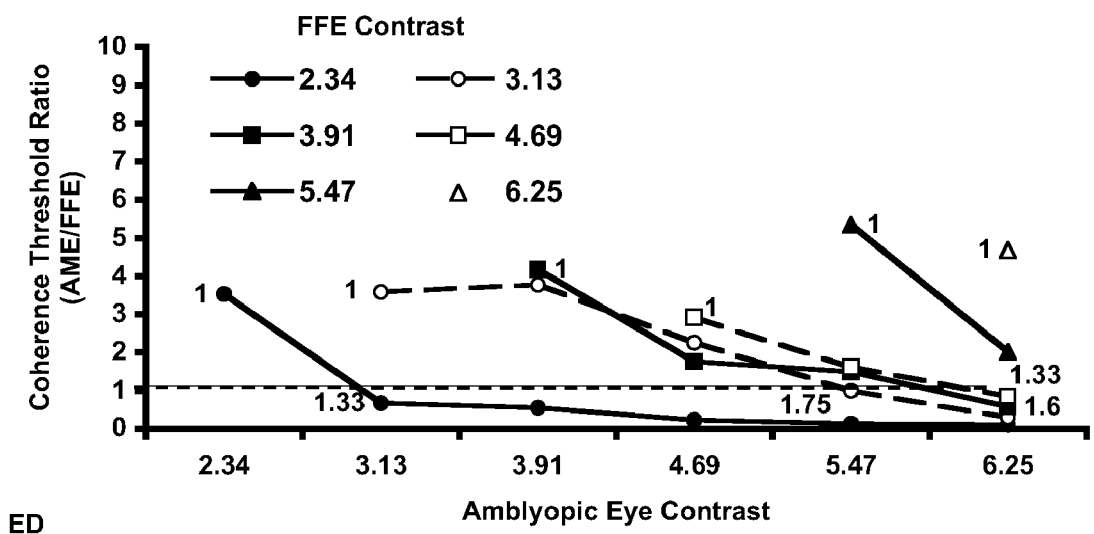
FIG. 3: Coherence threshold data for different combinations of contrasts to amblyoic and FFEs is represented for 4 individual subjects (A-D represent ED, GN, ML, and GC, respectively). The Y-axis represents the ratio of the AME to FFE coherence threshold. The X-axis represents the contrast of the stimuli, which were presented to the AME. The corresponding contrast of the stimuli presented to the FFE is presented as different curves (filled circle for 2.34%, open circle for 3.13% filled square for 3.91%, opened square for 4.69%, filled triangle for 5.475 and open triangle for 6.25%). The dotted line represents a ratio of 1 where the thresholds in both eyes are the same.
Figure 3B:
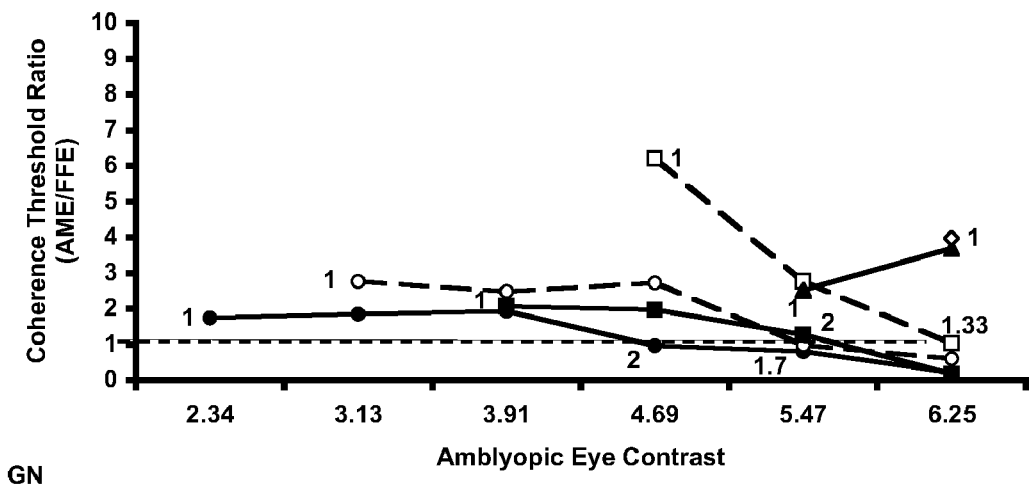
Figure 3C:
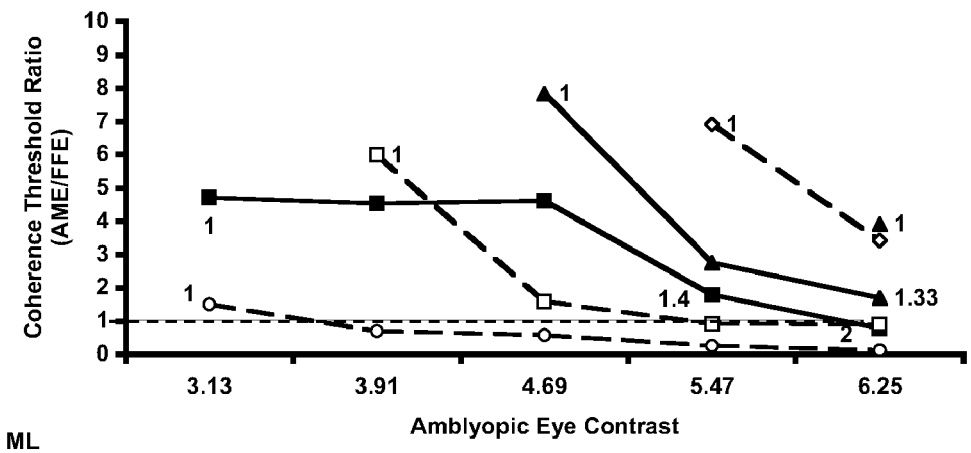
Figure 3D:
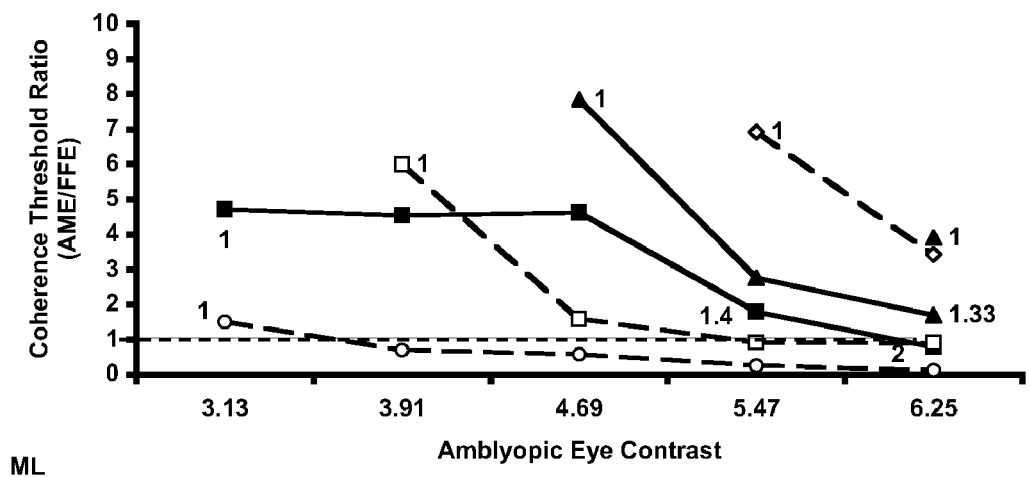
Figure 4:
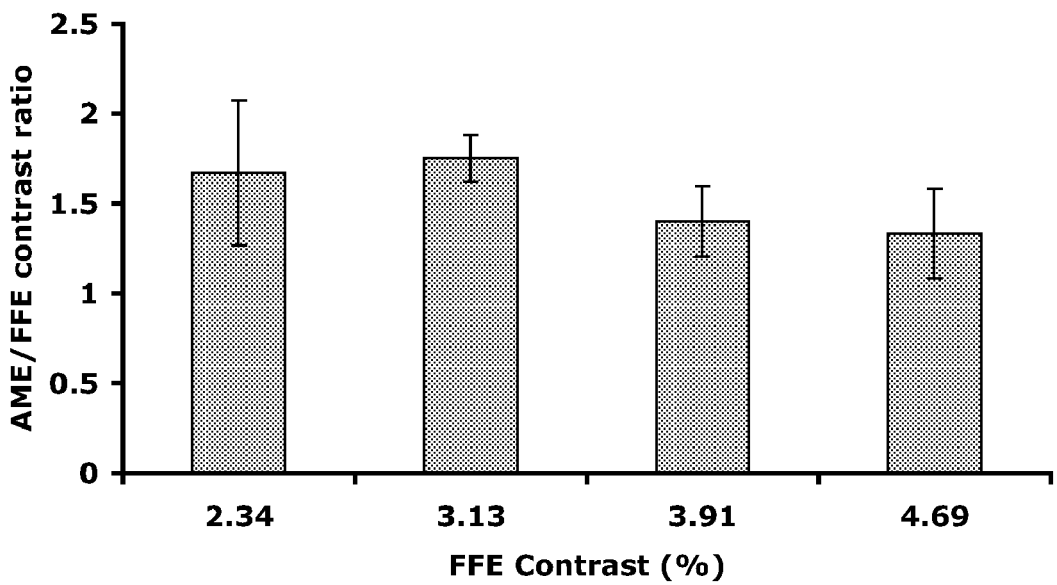
FIG. 4: The average contrast ratio of the fellow fixing to the AME when the coherence thresholds were equal in both eyes is presented in this figure. The X-axis represents the contrast of the stimuli to the FFEs and the Y-axis represents the contrast ratio of the stimuli to the AME and FFEs

FIG. 4 shows the ratio of the contrast of the stimuli presented to the AME and to the FFE when both eyes showed similar coherence thresholds. At all 4 different contrasts of the stimuli to the FFEs, AMEs needed more contrast (i.e. the ratio is higher than one) than the fellow eyes.

FIG. 5 shows the individual and average data for the amblyopic and non-dominant eye versus the corresponding value for the fellow fixing and dominant eye for monocular (A) and dichoptic (B) conditions. For the monocular condition most of the data points fall close to the dotted line (ratio of 1), although the filled squares (i.e. ratios for amblyopic subjects) are slightly higher than those of the normal subjects. This is also shown in the average data (i.e. big filled square versus big open square). However, the average for both data sets fall close to the dotted line which suggests that the FFEs and the AMEs are equally affected and have higher thresholds than those of the normal eyes.

For the binocular condition (B) however, the amblyopic data set is shifted up and to the left. The average data point for amblyopic subjects shows a shift to the left and above the average data point for the normal eyes. This suggests that the AME is much more defective than the FFE when those data are compared with those of the dominant and non-dominant eye.

FIG. 6 shows the average data for coherence threshold ratio in normal subjects' NDE over DE and for amblyopic subjects' AME over FFE for the dichoptic condition. For high contrast stimuli (e.g. over 6%) the ratio for normal subjects is close to one, which indicates a minimal difference in the performance of the DE and NDE at this range of contrasts. For AMEs however the differences in the performance of the AME versus the FFE is pronounced. At low contrasts (e.g. 3-5% contrasts) the AME difference remains constant but the normal eye differences decrease. At very low contrasts (e.g. below 3%) the NDE and AME show an almost similar deficit relative to the DE and FFE respectively.

Figure 7B:
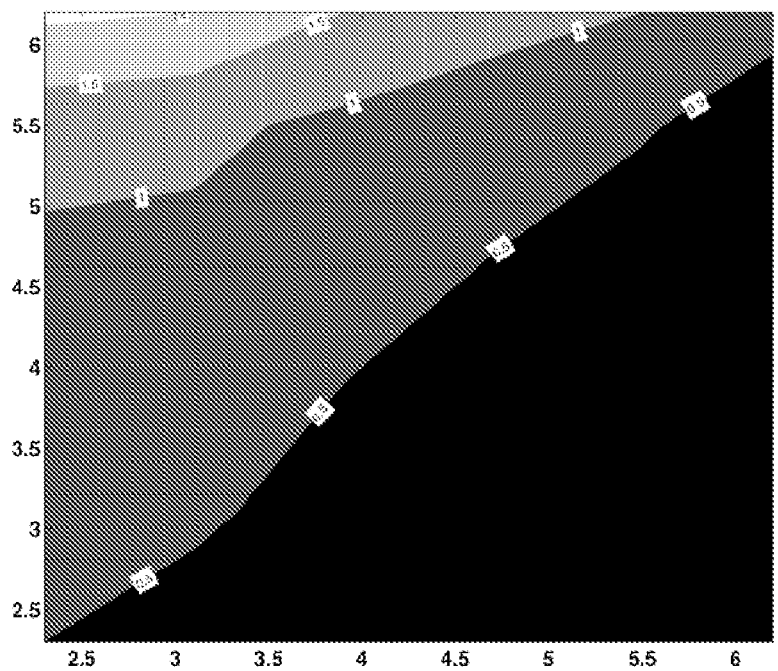
FIG. 7: The coherence threshold ratios of the AME over FFE for combinations of stimuli with different contrasts are presented for an ideal observer (A), monocular (B), and dichoptic (C) conditions. The X-axis represents the contrast of the stimuli to the FFE and the Y-axis represents the contrast to the AME. In (C) the average coherence threshold ratio of NDE to DE for normal observers for the dichoptic condition is represented on gray squares positioned along the diagonal axis where the contrasts of the stimuli were the same for both eyes.
Figure 7C:
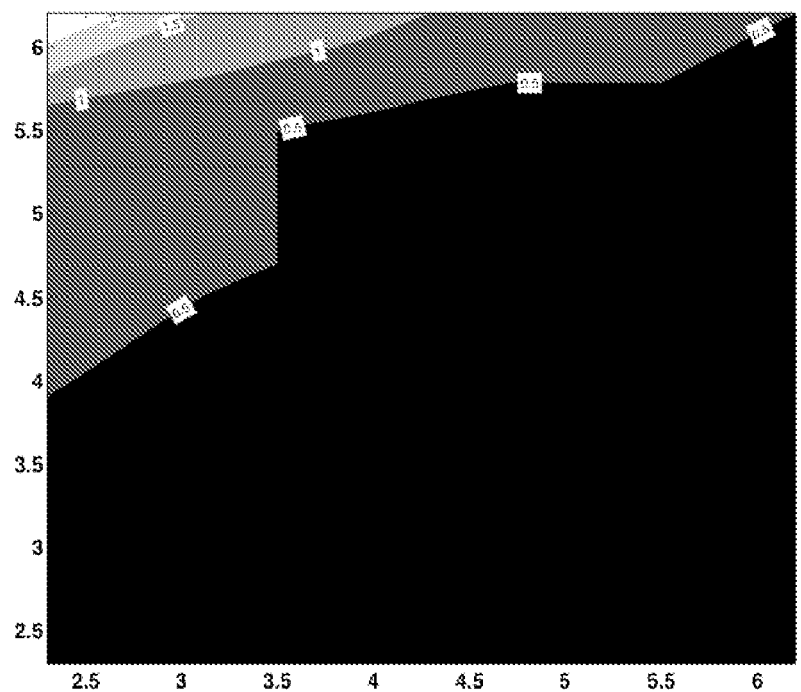

In FIG. 7 the coherence threshold ratios for the AME and FFE are presented with stimuli having different contrasts from a limited range (i.e. 2.5-6.5%). In (A) the data for an ideal observer is presented with the assumption that the information from the two eyes is linearly combined. The coherence thresholds are similar when the contrast of the stimuli to both eyes is the same and so the diagonal axis shows threshold ratios of one. Stimuli with higher contrast to either eye change the threshold ratio to the favor of that eye. In and monocular condition for amblyopic subjects (B) on the diagonal axis, where the contrasts of the stimuli to both eyes are the same, the ratios are 0.5 (on average), which indicates that the performance of the FFEs is twice as good as that of the AMEs. For equal performance (i.e. a ratio of one) the AME needs almost twice the contrast of that given to the FFE (e.g. 5 versus 2.5) to obtain similar performance. The amount of higher contrast required for similar performance of the two eyes decreases when the contrast to the FFE increases, however, there is a region of higher contrasts to the AME and lower contrasts to the FFE that provide similar performance for the two eyes. FIG. 7C shows the same plot as FIG. 6B, but for the binocular condition. The data shows that the curves are shifted up and therefore in order to have equal performance in two eyes, the AME needs much more contrast (5.7 versus 2.5). The average data for normal subjects under similar contrasts for both eyes is presented in grey squares along the diagonal axis. Unlike the ideal observer which has the ratio of one for corresponding thresholds from two eyes at the same contrasts, normal observers show better performance for DEs compared to NDEs when both are presented with the stimuli with the same contrasts. However the amblyopic subjects' ratios are dramatically higher than normals. Regarding the amblyopic subjects' data, there is still a region where the performance of the two eyes is similar under dichoptic presentation. There are even regions where the AMEs have better performance. This finding opens up a new opportunity for the treatment of amblyopia where under dichoptic presentation conditions, the AME can be activated.

In FIG. 8 the AMEs monocular performances are presented for when the FFEs are patched (open bars) and not patched (closed bars). The performance of the AMEs when FFEs are patched is better than when FFEs are open and presented with mean grey background. This is very important because it shows patching the FFE during psychophysical experiments slightly improves the vision in the AME and so partially conceals the AME deficiencies.

Experiment 2—Ventral Pathway Binocular Interactions

The results of experiment 1 indicated that binocular systems relating to dorsal visual processing are intact in amblyopia. As will be discussed in the following section, the treatment implications for this finding are significant. However any treatment targeting binocular function in amblyopia would not be satisfactory if only dorsal visual functions could be addressed. Applicants therefore applied the same dichoptic signal/noise paradigm to ventral stream processing in amblyopia. In Experiment 2, rather than motion information, applicants used small visual tokens (Gabor patches) each of which contained information at a specific orientation. One eye was presented with a signal population within which the orientation of each Gabor was randomly chosen from a population with predetermined mean and variance. The other eye was presented with a noise population within which each token had a random orientation. The task was to indicate the 'signal' orientation. With the same logic applied to Experiment 1, applicants reasoned that if the AME were presented with signal and the fellow eye with noise, complete suppression of the AME would lead to an inability to perform the task as only noise information would be available. However if any information from the AME was available to conscious perception, the amount of information could be objectively measured using psychophysical task performance. As in Experiment 1 applicants were able to independently manipulate the properties of each population of Gabors to control either the contrast or the physical number of Gabors presented to each eye (the 'number of samples'). Applicants found that the amblyopic visual system once again demonstrated intact binocular vision when either the contrast to the FFE was reduced, the number of samples was altered in favor of the AME or a combination of both. Once again the relative ratio of the information presented to each eye could be considered as an objective measure of binocular function in amblyopia that could not be predicted based on monocular differences in performance.

Apparatus (Exp. 2)

A Power Macintosh G3 computer was used to generate and display the stimuli. Stimulus presentation was controlled by the Matlab environment (MathWorks Ltd) and Psychophysics ToolBox (Brainard, 1997). All stimuli were displayed on a 20-inch Sony Trinitron GDM-F520 monitor for the disparity and control experiments. The monitor was calibrated and linearized using a Graseby S370 photometer and the Video Toolbox (Pelli, 1997) package. Pseudo 12 bit contrast accuracy was achieved by using a video attenuator (Pelli & Zhang, 1991) which combined the RBG outputs of the graphic card (ATI Rage 128) into the green (G) gun. The refresh rate was 75 Hz. The mean luminance of the screens was 28 cd/m$^2$. The resolution was 1152×870 pixels. One pixel on the screen was 0.32 mm, which was 2.12 arcmin of the observers' visual angle from the viewing distance of 52 cm.

Stimuli (Exp. 2)

Separate stimuli were presented to the left and right eyes, using a mirror stereoscope. Each eye viewed an independent image. These images were 6°×6° wide and arranged on the screen centrally and adjacent to each other. The left and right eye images were fused into one cyclopean image by the observer.

Stimuli were arrays of Gabor micro-patterns presented on a 30° (height)×38° (width) (from the observers distance) mean luminance background. The envelope of each Gabor had a standard deviation of 0.4 degree of visual angle. The spatial frequency of sinusoidal modulation within the Gabors was 0.52 cycles per degree (cpd). Typically, 16 Gabors were presented to each eye. These were positioned randomly within a circular area inside the box outline, centered on the center of the box. When the patches overlapped (as could occasionally occur), their gray levels were added, if this led to brightness levels outside the possible luminance range, they were clipped appropriately at the maximum or minimum contrast values.

The orientation of each Gabor was controlled by its parent distribution. Two types of parent distribution were used, producing two different Gabor populations: 'noise' and 'signal'. The orientation of each Gabor micro-pattern in the signal population was selected from a Gaussian distribution with a mean equal to the orientation cue (i.e. 90°± the cue generated by APE, an adaptive method of constant stimuli (Watt & Andrews, 1981) and a variable bandwidth. The distribution's standard deviation, $\sigma_{ext}$, was varied from 0° (all elements aligned) to 28° (high orientation variability). The orientations of Gabors in the noise population were selected from a Gaussian distribution with a standard deviation of 90°. Applicants used the same method to generate the parent distribution of the noise Gabors as were used to generate the parent distribution of the signal array. This meant that the noise population distributions had a randomly selected (on each trial) mean orientation, however, given the breadth of the distribution this was not discernable. Note also that since orientation is a circular variable (i.e. any orientation beyond 180° or below 0° is equivalent to its equilibrium in the 0° to 180° range), Applicants' noise populations were equivalent to uniform distributions between 0 and 180 degrees. Two different combinations of signal and noise were tested. Depending on which condition was tested, each eye's image could contain a signal population, a noise population or both. A stereoscope was used to show the left image to the left eye and the right image to the right eye. To prevent any bias, the observers were not informed which population (e.g. signal or noise) was being presented at any time and if different Gabor populations were presented to different eyes, the process was randomized within a run so that observers were unaware of which stimulus was presented to which eye. Observers did not receive feedback.

Two combinations of signal and noise were:

Signal population presented to FFE/DE and mean luminance to the AME/NDE, and vice versa (FIG. 9A).

Signal population presented to FFE/DE and noise population to the AME/NDE, and vice versa (FIG. 9B).

As stated above, all subjects started the experiment with the signal and noise populations each comprised of 16 Gabors and continued with different proportions of signal and noise and different contrast ratios for stimuli to either eye.

Procedure (Exp. 2)

A single temporal interval two alternative forced choice paradigm was used. The observers' task was to judge whether the mean orientation of the array of Gabors was rotated clockwise or counter-clockwise (tilted to right or left of vertical) (see FIG. 1). The stimulus presentation time was 500 ms in the main experiment. On each trial, observers indicated their decision with a button press. The mean orientation of the signal population was controlled by APE, an adaptive method of constant stimuli (Watt & Andrews, 1981) which sampled a range of orientations around vertical. Given that thresholds are estimates of response variance, the non-ideal behavior of observers with noiseless stimuli can be expressed as an additive internal noise. The level of internal noise is measured by increasing the amount of external noise in the stimulus and determining the point at which observers' performance begins to deteriorate. If the task requires integration, then observers' robustness to increasing amounts of external noise will depend decreasingly on internal noise and increasingly on how many samples are averaged. Thus the form of the equivalent noise model is:

$$\sigma_{obs}^2 = (\sigma_{int}^2 + \sigma_{ext}^2)/n$$

Where $\sigma_{obs}$ is the observed threshold, $\sigma_{ext}$ is the external noise, $\sigma_{int}$ is the estimated equivalent intrinsic or internal noise and n is the estimated number of samples being employed. In terms of the orientation discrimination task, $\sigma_{obs}$ corresponds to the threshold for orientation discrimination, $\sigma_{ext}$ to the standard deviation of the distribution from which the samples are derived, $\sigma_{int}$ to the noise associated with the measurement of each orientation sample and their combination and n corresponds to the estimated number of orientation samples being combined by the visual system. It is important to note that this is an equivalent noise model and that the model supplies equivalent estimated parameters. This is especially important in the later section where oriented noise populations (randomly oriented Gabors) are combined with signal Gabor populations. Orientation discrimination thresholds were derived from between 192-340 presentations for each of a number of standard deviations of the parent distribution i.e. external noise (10 levels typically between 0-28°. The orientation threshold for each level of variance of the parent distribution was estimated as the slope of the best fitting cumulative Gaussian function using a maximum likelihood procedure in which the threshold was equal to 82% correct (King-Smith & Rose, 1997). 1000 bootstrap replications of the fitted function were carried out and used to generate 95% confidence intervals (Cis) for the threshold estimates (Foster & Bischop, 1997). The orientation discrimination thresholds at each level of external noise were fitted by the equivalent noise model to derive the measures of internal noise and number of samples.

Results (Exp. 2)

FIG. 10 shows a condition where signal is presented to one eye at a time and mean luminance to the other eye (see FIG. 9(A)). The contrasts of the stimuli to the FFE and AME are set at a level that induces similar performance for the two eyes at the level of local orientation discrimination (e.g. 50% contrast to FFE and 75% contrast to AME for this example subject). So clearly if the AME is compensated for its contrast deficiency at local orientation level, it can perform the mean orientation task similarly to the FFE in a monocular presentation condition.

FIG. 11(A-D) shows different numbers of elements, which were dichoptically presented to one amblyopic subject (ML). In (A), 16 signal Gabors are presented to FFE and 16 noise Gabors to AME (circles and dashed line) and visa versa (stars and solid line) at a similar combination of contrasts as presented in FIG. 10 (50% to FFE and 75% to AME). The performance of the FFE when noise was presented to the AME is similar to when no noise was presented to AME. This suggested that at this condition, the noise through the AME has little effect in disrupting the performance of the visual system. On the contrary, noise through FFE can completely disrupt the performance of the visual system when signal Gabors are presented to the AME. This is very interesting because both eyes showed similar performances when tested with similar stimuli but under monocular conditions (see FIG. 10). The disturbed performance of the AME is demonstrated by high thresholds as well as high levels of internal noise and lower sampling efficiency, as derived from fitting the equivalent noise model to the threshold data (see Methods). Internal noise parameters increased by a factor of 10 (i.e. 1.6 in FIG. 10, to 16.7) and sampling efficiency diminished from 3.9 to 0.5.

In FIG. 11(B) the number of elements to the FFE is reduced to 8 and to the AME increased to 32. Although this different number of elements slightly improved the performance of the AME, there was still a large difference in the performance of the two eyes. In some subjects such as ED, though, this ratio of different number of samples was enough to equalize the performance of the two eyes. In FIG. 11(C) the number of elements to the FFE is 4 and to the AME is 64. At this ratio, the performance of the two eyes in this individual subject were similar which is reflected in both the thresholds and the model parameters (IN=1.9 and 3.6 and NS=2.5, 3.9 in FFE and AME, respectively). This suggests that originally the visual system didn't combine the information, which was presented dichoptically to two eyes. Instead, the visual system ignored the AME even when it contained the useful information i.e. signal Gabors. However, when stronger information was presented to the AME, the visual system fused the images from the two eyes, which shows that the binocular system was activated. In FIG. 11(D) applicants pursued the process of increasing the number of elements to the AME whereby 128 Gabors were presented to the AME and 2 elements to the FFE. The performance of the AME continues to improve over that of FFE which is specially reflected in the high standard deviations and sampling efficiency (i.e. NS=1.2 and 9.1 in FFE and AME, respectively). Therefore the dominance of the FFE over AME is not absolute. It is possible to create artificial circumstances where the AME has dominance over the FFE.

Figure 12B:
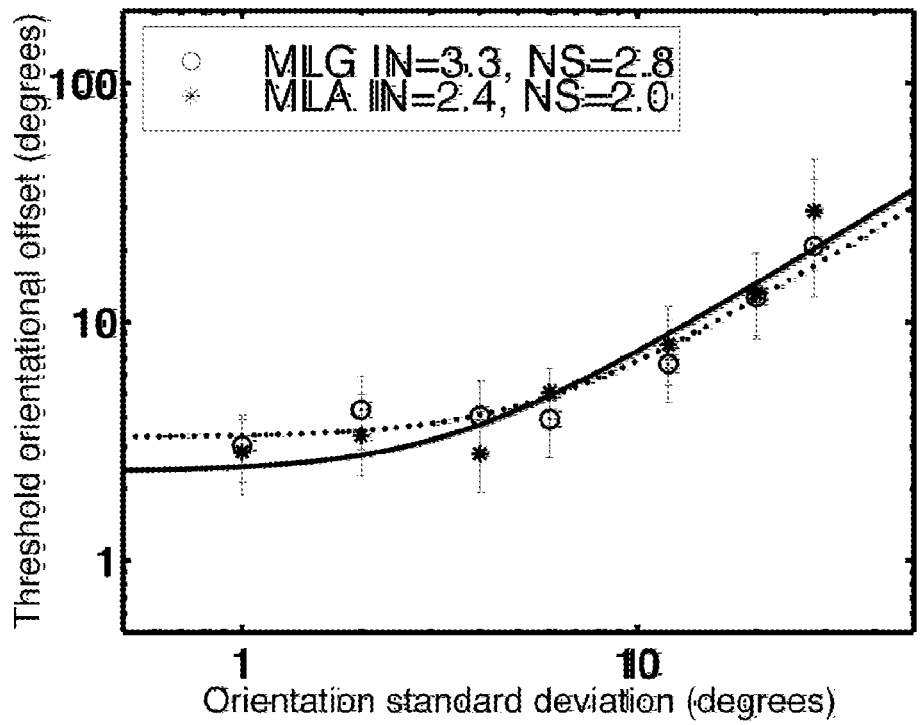
FIG. 12: Mean orientation discrimination thresholds are presented for FFE (circles and dotted lines) and AME (stars and solid lines) for AME/FFE contrast ratio of 75% to 25%, 75% to 10%, and 75% to 5% for A-C, respectively. Internal noise (IN) and sampling efficiency (NS) parameters are presented in insets. The X-axes represent orientation standard deviations (°). Y-axes represent threshold orientation offset (°).
Figure 12C:
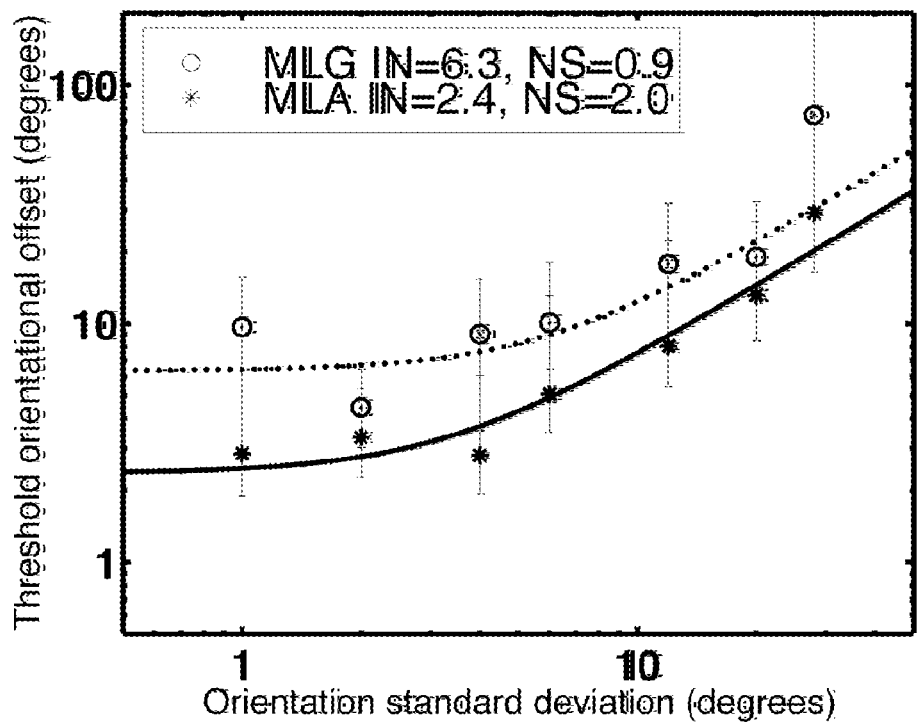

FIG. 12(A-D) shows conditions where the number of the stimuli to both eyes and contrast of the stimuli to the AME is kept constant (i.e. 16 Gabors and 75%, respectively) and the contrast of the stimuli to the FFE is reduced to 25% in A, 10% in B and 5% in C. Reducing the contrast to the FFE to 25% improves the performance of the AME (IN in AME equals to 16.7 in FIG. 11(A) when contrast of the stimuli to FFE is 50% compared to 6.0 in FIG. 12(A) when that is 25%). This suggests that there is an inhibition from the FFE over the AME (i.e. suppression) that can be reduced by reducing the relative contrast to the FFE. In (B), reducing the contrast of the stimuli to the FFE to 10% was enough to equalize the performance of the two eyes. Greater reduction in contrast of the stimuli to the FFE results in better performance of the AME compared to that of the FFE (IN=6.3 and 2.4 in FFE and AME, respectively (FIG. 12(C)).

FIG. 13 shows internal noise (A) and sampling efficiency (B) parameters in 5 amblyopic subjects who completed the condition where the number of elements was changing. Internal noise increased and the number of samples decreased dramatically in the amblyopic eyes when monocular presentation was changed to binocular presentation even when a similar number of elements were presented to the two eyes. The internal noise in FFEs however, did not change. When the ratio of number of elements presented to the AME to those presented to the FFE decreased, internal noise in the AME became closer to the internal noise in the fellow eye. The behavior of the sampling efficiency parameter was not consistent in all observers. Generally however, it decreased in AMEs for the binocular presentation condition. When the ratio of the number of elements presented to two eyes changed (i.e. decreased), the sampling efficiency changed accordingly and became closer to that of the FFEs.

Figure 14A:
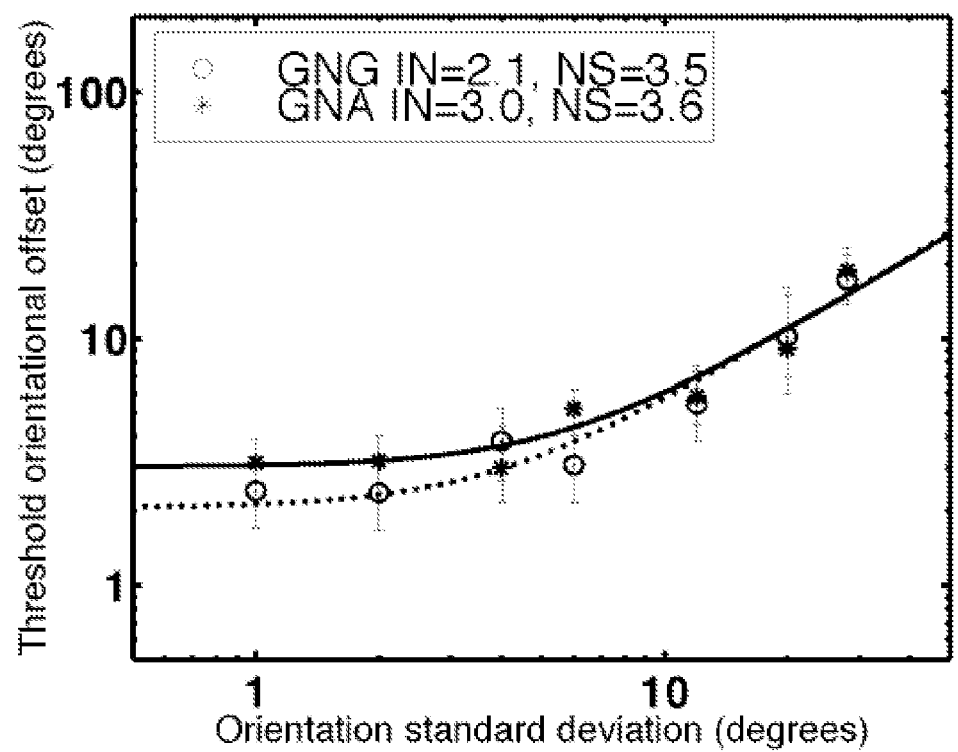
FIG. 14: The mean orientation discrimination thresholds for one amblyopic subject (GN) is presented for matched contrast monocular condition (A) and combinations of different number of elements and contrasts to AME and FFE (B). In (B) the number of elements changes from 16/16 to 2/128 along the horizontal axis and the contrast from 25/75 to 5/75 along the vertical axis. Combinations of changes in number of elements (i.e. FFE/AME from 16/16 to 2/128) and contrast (FFE/AME from 25/75 to 5/75) brought the performance of the AME and FFE close to each other.
Figure 14B:
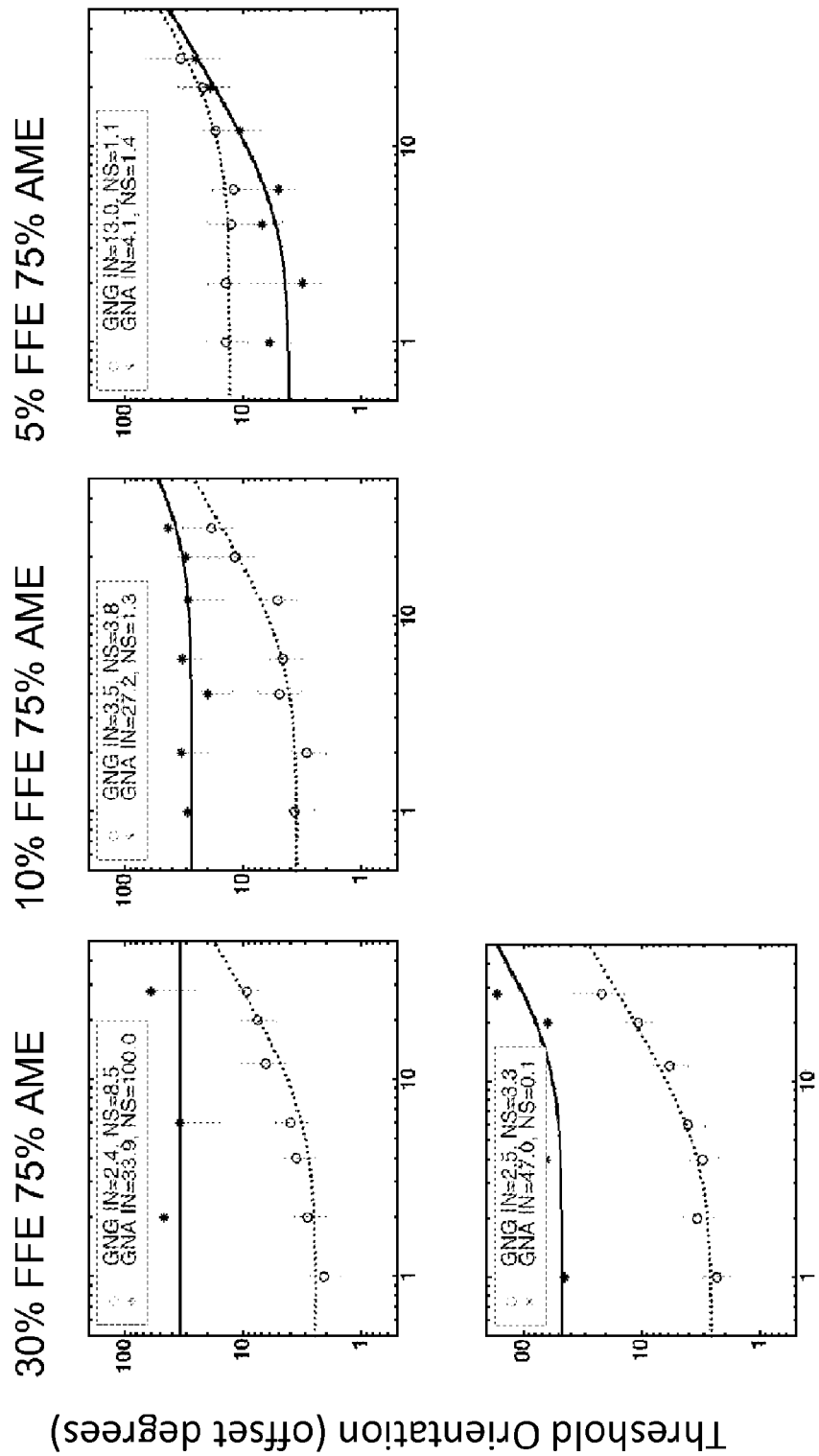
Figure 14B:
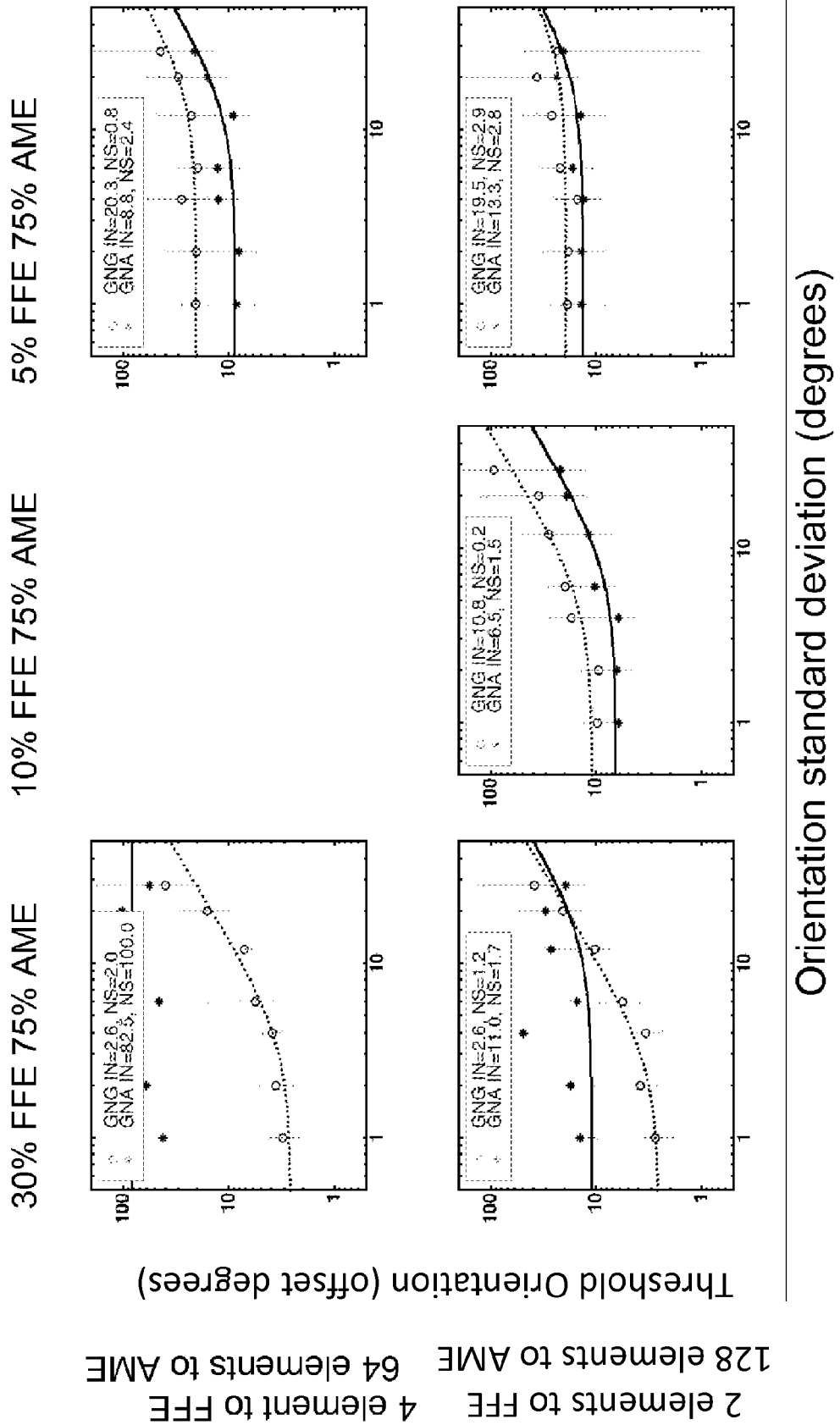

FIG. 14 shows combinations of different numbers of elements and contrast in one sample observer amblyope. FIG. 14(A) is the reference monocular condition where both eyes showed similar performances when 16 signal Gabors were presented to either of them with 30% contrast to FFE and 75% to AME. FIG. 14(B) shows the variations of number of samples and contrast and combination of the two. It is shown for this subject that changing each variable alone brings the performances of the two eyes close to each other but it is not enough (at least at the ranges applicants used) to equalize the performances. However when two variables were changed together, the performance of the two eyes became similar.

GENERAL DISCUSSION

The results from Applicants' dorsal and ventral pathway investigation clearly demonstrate that under certain, 'balanced' conditions, the amblyopic visual system can support binocular interactions. The ratio of contrast that is required to each eye to achieve this balancing may also be considered as an objective measure of the amount of inter-ocular inhibition present in a particular patient's visual system. This contrast ratio which leads to binocular matched performances of AME and FFE cannot be predicted from a knowledge of the monocular contrast ratios, demonstrating that the suppression present in the amblyopic visual system needs to be measured individually when assessing AME function and also in clinical assessments of treatment outcomes. Highlighting this point is the current finding that AME monocular performances were influenced by whether the FFE was patched or unpatched and viewing mean-luminance grey. Therefore measures of AME function when the fellow eye is patched are almost certainly underestimating the visual deficits present in the AME under normal, binocular, viewing conditions.

Highlights of the Applicants' Study are:

Binocular interactions in amblyopia: Applicants have shown that in all the amblyopic observers tested, the binocular system, whilst weak was intact. This was true for both the dorsal and the ventral processing streams.

Implication of this method in treatment: Applicants' results have significant implications for the treatment of amblyopia. The fact that it is possible to artificially create conditions where AME has dominancy over FFE, is very important for treatment of amblyopia for two reasons. First, this shows it is possible to activate AME without any need to patch or penalize the FFE. Second, under these conditions the visual system fuses the information from two images presented to AME and FFE, which shows that the binocular system is active in amblyopia. Stereopsis, which is lost in most strabismic amblyopes, requires binocular vision and the fusing of images from the two eyes. Although activating the binocular system in amblyopes does not necessarily lead to stereopsis, training the amblyopic visual system binocularly, might restore the stereopsis in amblyopia, in spite of the evidence that shows that stereopsis improves even under monocular visual training i.e. patching (Mitchell, Howell & Keith, 1983).

Furthermore, there is evidence that some higher order functions in amblyopia are not developed, even for the FFE which has normal monocular vision. The loss of function in the FFE is hypothesized to be due to deficits in binocular function. Therefore, restoring binocular vision might help the amblyopic visual system restore such mechanisms.

Applicants' rationale for developing a game for the treatment of visual disorders involving binocular vision stems from multiple requirements that such a game satisfies. First, system operation must be sufficiently straightforward that ease-of-use is not an obstacle. Second, the game itself should be compelling and motivate use more so than a traditional therapeutic task if it is to be used regularly outside of the clinic. This is particularly relevant for children, as compliance is a major issue for current treatments of childhood amblyopia. However, despite the prevailing opinion that treatment of amblyopia is only effective in children, Applicants initial results show promising effects for adults.

The apparatus and method described by Applicants is novel approach to the assessment and treatment of amblyopia, which overcomes many of the problems described above.

AN ALTERNATIVE CONTRAST-BASED APPROACH TO TREATMENT OF AMBLYOPIA. Applicants novel approach to this problem was motivated by the observation that if visual stimuli are presented separately but simultaneously to each eye, in a manner that sufficiently favors the amblyopic eye (e.g., by reducing image contrast to the non-amblyopic eye), at a certain "balance point" of contrasts, both eyes contribute to visual perception. Determining this balance point of contrasts is necessary for optimum cooperation between the eyes, and hence, successful treatment. The result of improving the cooperation between the eyes is that the degree of amblyopia reduces.

Consider an extreme case when the contrast to the fellow eye is reduced all the way to zero, and the contrast to the amblyopic eye is set at the maximum limit of the display. This scenario becomes analogous to applying a patch over the good eye, thus channeling all incoming visual information through the weaker eye. In other words, the amblyopic eye would then dominate the visual system. However, if Applicants gradually increase the contrast seen by the fellow eye towards the balance point threshold (FIG. 17), then it has been previously shown that the brain combines information, shifting from a dominant-eye condition to an equilibrium where both eyes contribute to the visual process. Unequal contrasts are required to maintain this equilibrium, with higher contrast to the amblyopic eye and lower contrast to the fellow eye.

Figure 17:
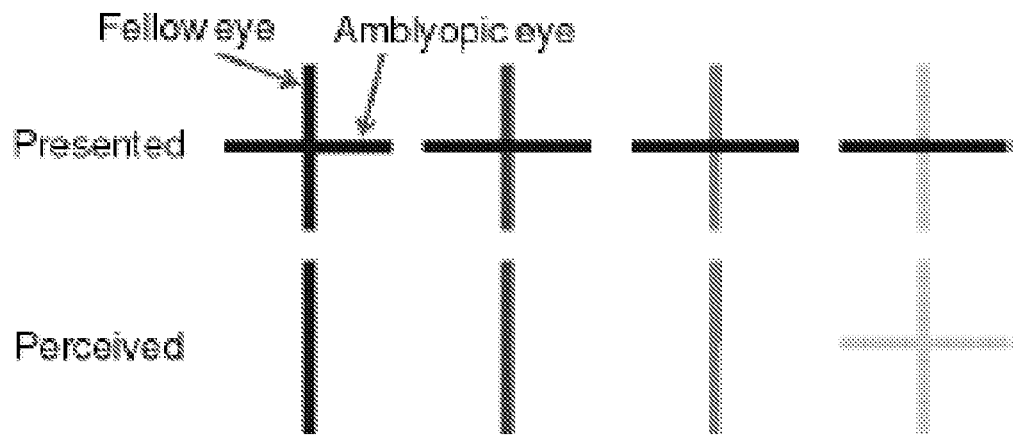
FIG. 17 is a simplified schematic representation of the balancing procedure using contrast to balance the images of the two eyes in amblyopia.

A simplified schematic representation of the balancing procedure using contrast to balance the images of the two eyes in amblyopia is shown in FIG. 17. When two lines, one horizontal and one vertical are presented to each eye of a normal observer a cross is perceived as the lines are binocularly fused. This is not the case for an amblyope where, due to suppression, only the line presented to the fellow fixing (non-amblyopic) eye will be perceived (compare top row that shows the presented stimuli with the bottom row that shows the amblyope's percept). However, if information presented to the fellow eye is weakened (in this case the line is reduced in contrast) the amblyopic visual system can overcome the suppression and binocular vision can be achieved. The relative contrast between the eyes at this point is the "balance point" where suppression is no longer sufficiently strong to inhibit binocular combination.

If Applicants continue to increase the fellow-eye contrast beyond this level, the subject will eventually return to the amblyopic viewing habit, i.e., suppressing the information received by the weaker eye. Thus, for therapeutic effect, Applicants must devise a way to change the subject's balance point, gradually moving to equal contrast between the two eyes while still maintaining the visual equilibrium condition across the eyes.

The proposed treatment method has the subject observe a visual stimulus at the balance-point contrast for a period of time, and then increases the difficulty of the task by slightly raising the fellow-eye contrast. This procedure makes it possible, after sufficient treatment, to reach an equal-contrast viewing condition, as the subject continuously adapts to maintain the equilibrium perception from both eyes as the contrast ratio changes.

Figure 18:
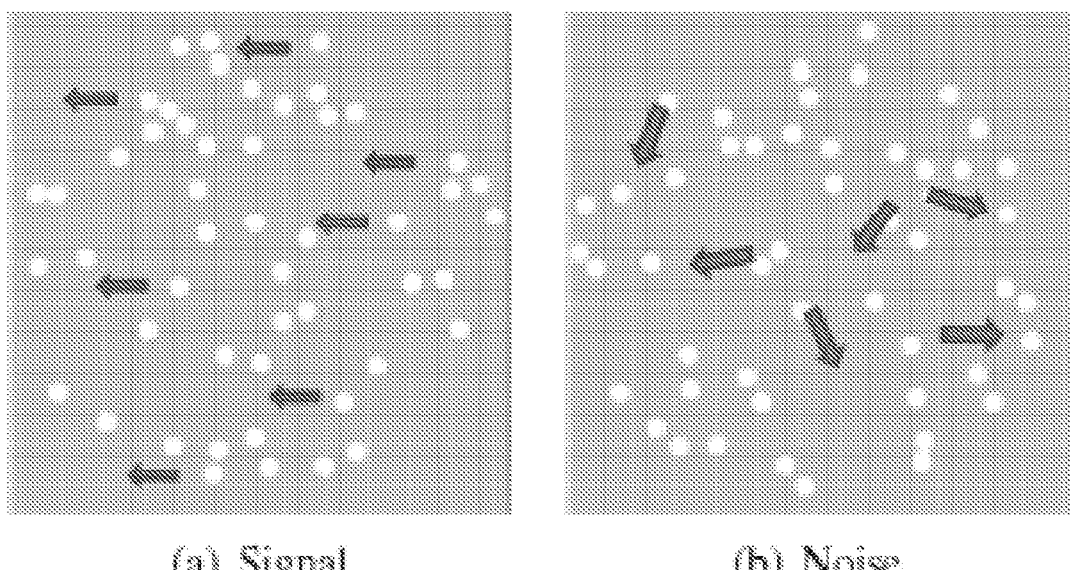
FIG. 18 is a schematic representation of the dot stimulus paradigm, with all signal dots moving in the same horizontal direction for the amblyopic eye (a) and noise dots moving in random direction for the fellow eye.

As the severity of amblyopia varies amongst subjects, it is necessary to establish the contrast ratio for each subject individually. The question is how much to lower the initial contrast for the fellow eye so that the amblyopic eye will function equally well. The performance of each eye is measured by its ability to detect a signal in the presence of random noise (or signal-to-noise ratio). Signal and noise are represented by two set of dots, where all the signal dots move in the same horizontal direction and the noise dots move in random directions (FIG. 18). The performance is quantified as the minimum number of signal dots needed for the subject to detect the signal reliably, despite the presence of added noise.

Dot stimulus, with all signal dots moving in the same horizontal v direction for the amblyopic eye FIG. 18(a), and noise dots moving in random directions for the fellow eye FIG. 18(b). To engage the amblyopic eye, the contrast ratio is set to the balance point where the signal dots have a higher contrast.

Applicants assign the subject a task requiring the integration of the information presented to the two eyes, in this case, indicating the direction of the moving dots. Using this technique, an objective binocular visual assessment tool was developed by Mansouri et. al. Through repetitive image presentation sessions under balanced conditions, an improvement in the combination of visual information between the eyes was observed. Moreover, this new treatment has been validated with adult subjects, whereas previous treatments for amblyopia were only (partially) effective for children, when the visual system is still under development.

Using a two-alternative forced choice response method, such an experiment requires minimum interaction by the observer, only asking whether the stimulus movement is to the left or to the right.

Whereas other treatments only deal with monocular loss and accordingly have a high relapse rate, Applicants technique also directly addresses the binocular suppression that underpins much of the visual loss in the amblyopic eye.

DESIGN CONSIDERATIONS. From a design perspective, the underlying principle for the rehabilitation process is to exploit a contrast difference to coerce the two eyes into cooperating to complete a visual task. For reasons elaborated upon below, the simple dot stimulus is unsatisfying as a long term treatment stimuli. Instead, Applicants adopted an implementation of a modified Tetris game on a mobile device for this purpose.

Mobility. Since treatment of this form is likely to offer superior results with frequent exposure, scheduling considerations for the clinician, patients, and parents (of children being treated) favour a solution that does not require administration in the office of a vision care practitioner. In order to deliver the treatment effectively, reach the maximum number of patients, and compete with monocular approaches, a take-home device is imperative. In taking this balanced-contrast treatment outside the environment of a vision laboratory, Applicants envision that the new platform should be compact and mobile, allowing users to carry it easily and use it at their convenience.

Applicants are then faced with the question of how to send the different contrast images to each eye. Prior options investigated in the lab included a CRT monitor with either a view barrier between the two eyes or using a mirror stereoscope or a less constraining head-mounted display. Similarly, polarized glasses, anaglyph glasses or shutter glasses technology, coupled with an appropriate screen display, could be considered. However, these possibilities seemed less suitable for supporting mobile play, maximizing portability, gaining user acceptance of the technology, and minimizing cost for the additional hardware.

Figure 19:
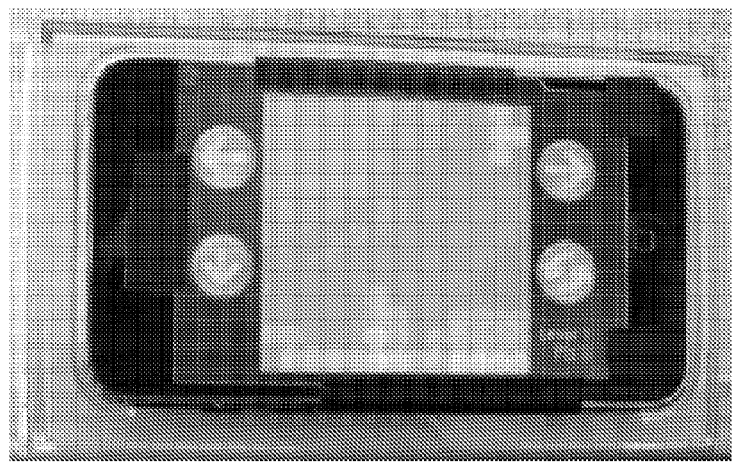
FIG. 19 shows the game prototype using an iPod Touch with an overlay lenticular lens, which provides different content to each eye.
Figure 19:
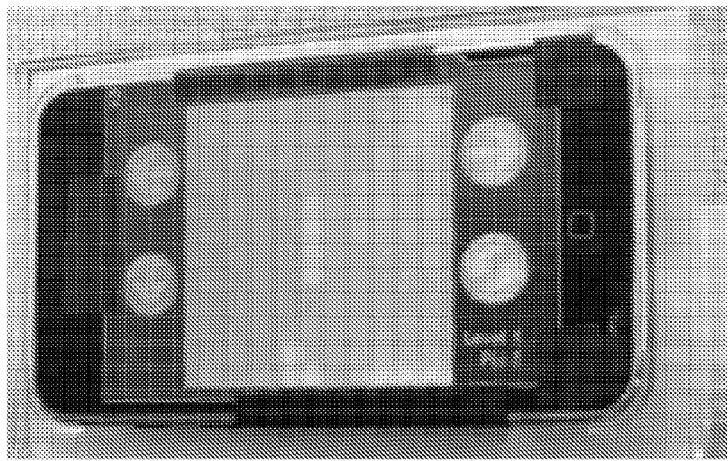

The game prototype using an iPod Touch (as shown in FIG. 19) with an overlay lenticular lens, which provides different content to each eye. The two pictures are presented simultaneously, but each is only visible to a specific horizontal viewing angle. FIG. 19(a) Fellow eye: Static tetris blocks buried below other blocks at the bottom of the gameboard are fully visible to the strong eye, while the more relevant "uncovered" blocks at the bottom of the screen are displayed in low contrast. FIG. 19(b) Amblyopic eye: The falling tetris is only visible to the weaker eye, which also sees some the buried blocks at the bottom of the gameboard. All the information sent to the amblyopic eye is in high contrast. Ideally, Applicants wanted to avoid the need for special eye gear of any form. This motivated Applicants adoption of display technology based on the characteristics of a lenticular array surface, placed overtop of an LCD display (FIG. 19).

Figure 20:
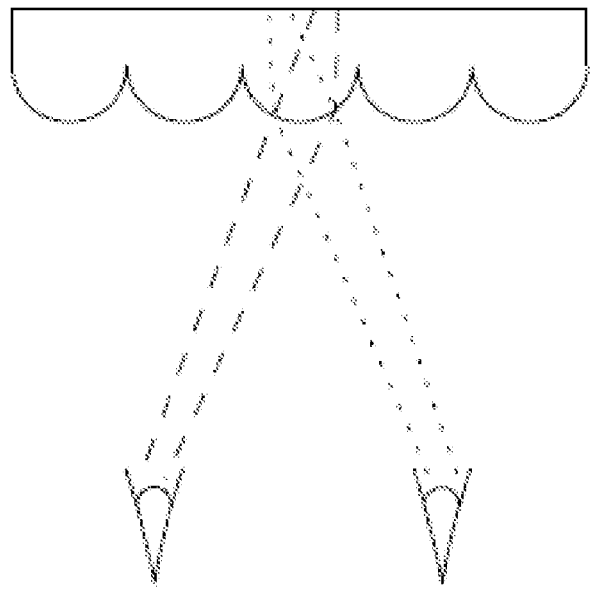
FIG. 20 is a schematic representation of a lenticular overlay device for rendering separate images to the two eyes.

The lenticular sheet consists of a series of small cylindrical lenses, through which the underlying image is divided into interleaving stripes, visible at different viewing angles (FIG. 20). This principle, popularized in Cracker Jack prizes from the 1950s, is used for rendering separate images to the two eyes using a lenticular overlay and results in the appearance of different images as either the display surface or the viewer changes angle. Because the viewer does not need to wear any special eye gear, the exercise is less strenuous over an extended period of use.

In a more modern context, this technique is employed to achieve auto-stereoscopic displays, which provide stereographic (3D) effects to viewers without the requirement of special eye gear. In Applicants case, stereopsis is not the intended (or at least, the primary) effect, but Applicants can exploit the same technology to provide the appropriate differentiated presentation of information to the two eyes.

Ease of setup. While special-purpose software and hardware can be used in a lab environment, use of the device should require zero-to-minimal setup effort. Applicant's hardware prototypes are self-contained systems that can easily be held in the hands even during long sessions. No additional hardware such as special glasses or positioning mechanisms is required. The platform used in Applicants experiments is an Apple iPod Touch device, which can be run on battery for many hours and is sufficiently light and small to be carried easily and used throughout the day as time permits, avoiding the need for scheduling specific times and locations for the therapy.

One of the drawbacks of the iPod Touch, however, is that movement of either the display or the user's head can impair the effect of the lenticular overlay since it is highly dependent on viewing angle. At an incorrect angle, there is significant bleeding of the image for the left eye into the right, and vice-versa. With enough of a horizontal shift, the signals to the eyes may be swapped completely, thus negating any therapeutic effect. Other devices, such as the Sony UMPC used for Applicants second handheld prototype, are significantly larger and heavier, but have an integrated front-facing camera that can be used to track the user's eye position relative to the screen.

Using this information, the image behind the lenticular material can be adjusted to compensate for the user's changing eye position relative to the screen, reducing or eliminating the problem of display bleeding between the two eyes. Since front-facing cameras are an increasingly common option on handheld devices, Applicants expect this to be a viable option for a future commercial system.

User Engagement. Although the dot stimulus on which the approach was first validated demonstrated initial success, Applicants wanted to apply this to a more engaging and pleasant activity that would encourage usage, and hence, reduce or eliminate the compliance issues noted above. For this reason, Applicants were motivated to adopt a game as the visual task. Significantly, the game paradigm ensures that the user is engaged as an interactive participant, rather than being limited to passive observation, as was the case in the dot stimulus paradigm.

Inspired by a recent study showing that a prolonged period of Tetris playing can lead to changes in the temporal pole, a brain area that integrates visual information, Applicants decided to adopt a modified Tetris game as the visual task.

Tetris is a popular and simple game that is easy to learn. While the previous dot-based experiment provides only two alternative forced choices (2AFC), left and right, Tetris players interact continuously with controls for rotating the falling Tetris blocks and shifting them left and right. Moreover, the block-based construction of game elements provides a convenient framework to customize the visibility and contrast on a block-by-block basis.

Figure 24:
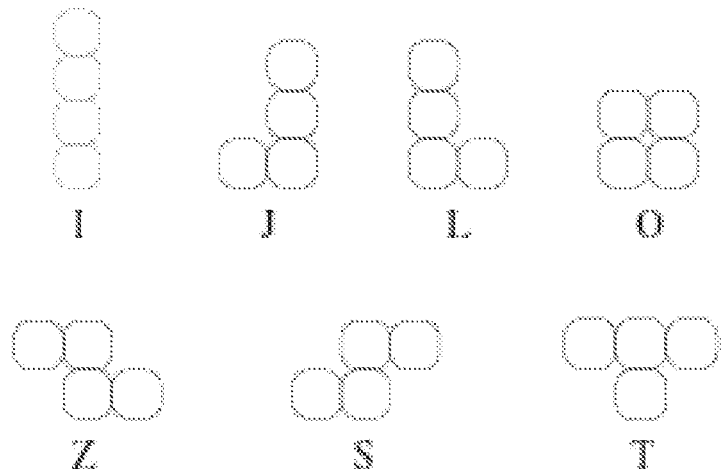
FIG. 24 is game design #1 where falling Tetris pieces in high contrast to the amblyopic eye and bottom rows are sent in low contrast to the fellow eye.
Figure 25:
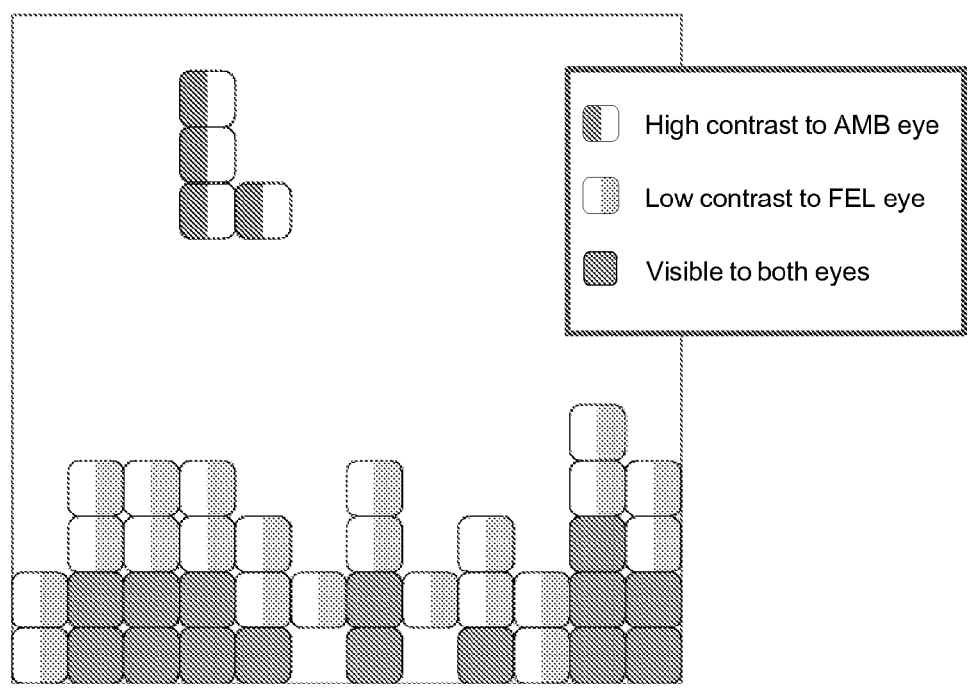
FIG. 25 is game design #2 where falling Tetris blocks are split between the two eyes.
Figure 26:
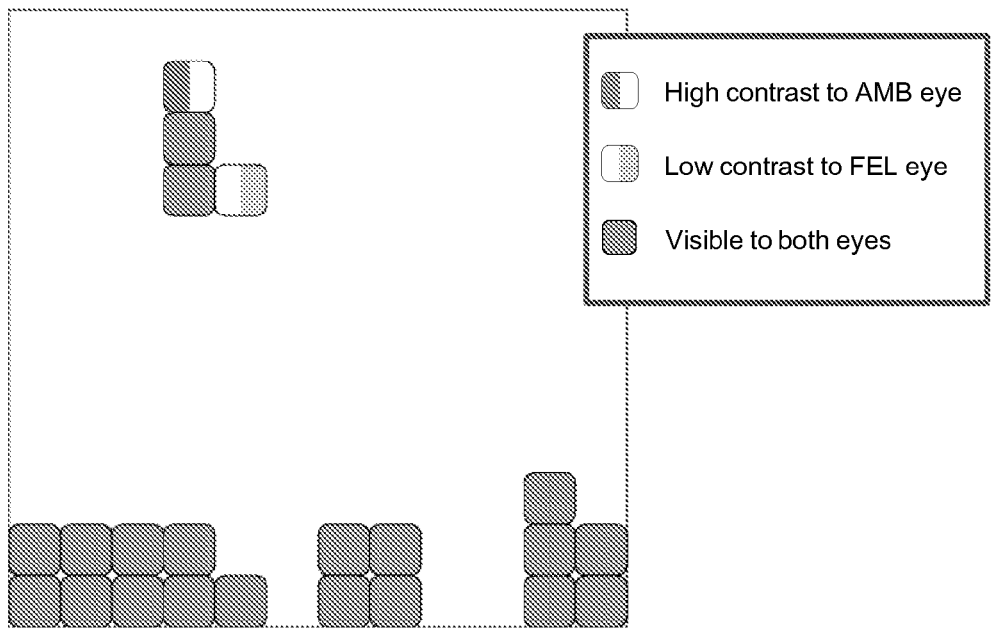
FIG. 26 is game design #3 using random noise sent to the fellow eye.

The game requires a player to align various falling elementary shapes, shown in FIG. 24, which randomly appear one at a time at the top of the screen. The objective is to form complete rows of blocks as the pieces reach the bottom of the screen. This task relies on the ability to see and combine the shape and orientation of the falling Tetris with the gaps in the partially completed rows at the bottom of the screen. In addition, Tetris can be played by an amblyope (or a person with anomalous binocular vision such as a strabismic) as it does not require stereo vision. However, an amblyopic player would ordinarily perceive the game only through the good eye due to suppression. To elicit cooperation between the eyes, the graphical contents of Applicants modified Tetris game are partitioned as follows. Some content is sent to the amblyopic eye at high contrast, a second group is sent to the good eye at reduced contrast, and a third set is sent to both eyes at high contrast.

Figure 21:
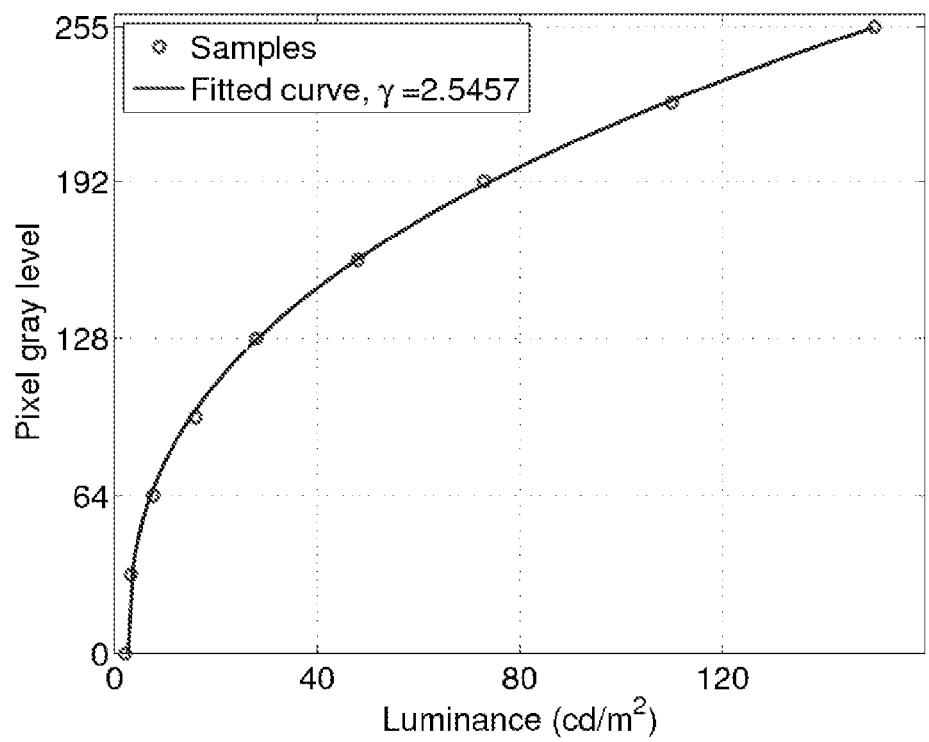
FIG. 21 is a graphic representation of luminance vs. pixel gray value.

SYSTEM IMPLEMENTATION. Screen calibration and contrast presentation. The game is implemented completely in grayscale by setting the red, green and blue values of each pixel to be equal, effectively turning the iPod Touch into an 8-bit grayscale device. The luminance of the iPod Touch display is approximated by the following equation, after gamma estimation. The unit of luminance is cd=m$^2$.

$$L_y = L_0 + (L_{255} - L_0)(y/255)^\gamma \tag{1}$$

where y $\Sigma[0; 255]$ is the pixel grayscale value, $L_0$ is the minimum luminance when all pixels are set to black, and $L_{255}$ is the maximum luminance when all pixels are set to white. The value $\gamma$ is estimated by first sampling the display luminance with a spot photometer at discrete pixel values from 0 to 255, with interval of 32 between samples, and then fitting a curve through the data points as illustrated in FIG. 21.

Contrast of a game element is defined by the relative luminance of a Tetris block against the uniform background of the gameboard. The contrast value is calculated as follows:

$$C = (L_{tetris} - L_{background}) / L_{background} \tag{2}$$

The background luminance is set to half of the maximum output luminance, i.e., $L_{background} = L_{max}/2$, where $L_{max}$ is the screen luminance where all pixels are set to 255. The foreground luminance is determined respectively from the contrast levels seen by the amblyopic and fellow eyes. The amblyopic-eye foreground luminance is kept at Lmax to maintain the highest contrast. For the fellow eye, the contrast corresponding to the balance point is used to calculate the luminance, which varies between $L_{background}$ and $L_{max}$.

Software. The game software is written in Objective-C using the iPhone software development kit. Applicants use OpenGL (ES) for rendering, and all game controls are handled inside the OpenGL drawing loop. The image processing technique to interlace the images sent to the left and right eyes into a single image for display on the iPod Touch is provided by a proprietary rendering engine from SpatialView Inc.

Figure 22:
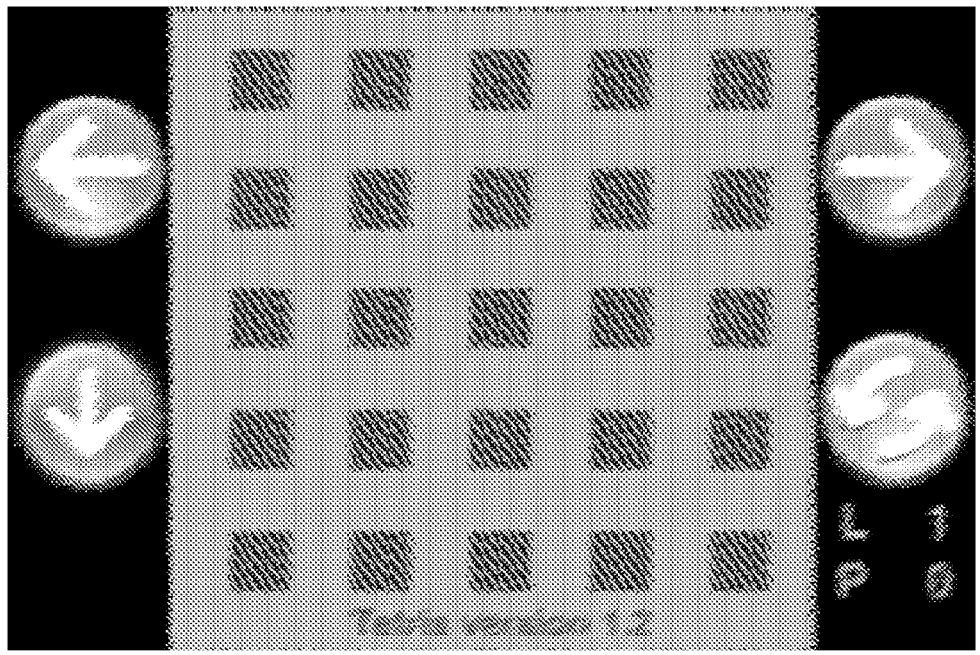
FIG. 22 illustrates a screen capture used for the calibration of information for the two eyes (i.e. eye alignment).

FIG. 22 illustrates a screen capture showing the calibration of information for the two eyes. The user must move the device back and forth and change the horizontal angle of the screen until they see only green squares in one eye and blue squares in the other. The lenticular overlay separates the information between the two eyes, but it must be correctly aligned with the surface of the display prior to use to prevent bleeding of information between the two eyes.

Figure 23:
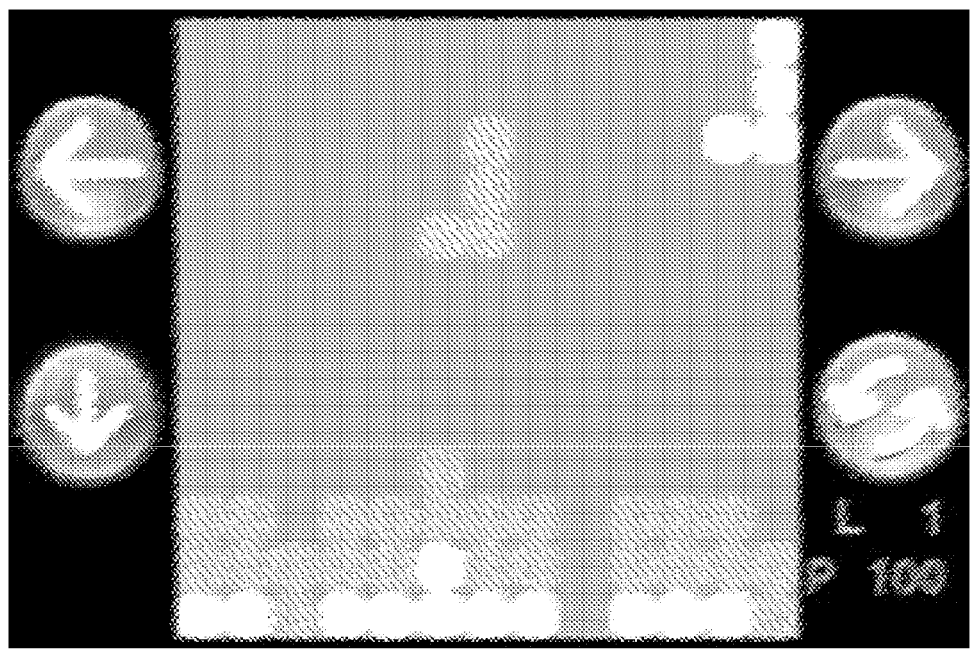
FIG. 23 is an illustration of all possible Tetris pieces.

FIG. 23 shows a sample Tetris screenshot during a game, without the lenticular layer. Note the falling Tetris and top two blocks in each column at the bottom of the screen are striped such that the lenticular material sends the block to only one eye. In this example, the falling block is visible only to the amblyopic eye, whereas the striped blocks at the bottom of the screen are visible only to the fellow eye. The latter group is also dimmer, resulting in these blocks having lower contrast in order to engage the amblyopic eye.

For Applicants initial field test, the user's head was fixed in a chin rest to ensure that it did not change position as they played the game. In addition, instead of implementing the game's control buttons on the iPod Touch's touchscreen, a wireless connection to another computer was used to allow remote control of the game through a standard keyboard, thus minimizing the risk of display movement relative to the user's head.

In commercial systems, Applicants could use either the touchscreen itself for game control, or find a device with built-in hardware gaming controls. Several factors encourage optimism that this will be possible, despite the increased difficulty a user will experience trying to maintain the correct head position and angle relative to the screen while also manipulating controls located on the device. First, the lenticular material has improved significantly, just within a one year time frame of Applicants initial development, with a much greater tolerance for small shifts in viewing angle. At this point, Applicants believe it is likely that a cooperative user who makes an effort to maintain the correct angle while playing, coupled with regular verification operations to ensure that the viewing angle is still correct, will achieve a therapeutic effect. Second, adding support for eye-tracking via a front-facing camera on the device would dramatically reduce the sensitivity to view angle, as the rendering engine can compensate for such changes. Third, Applicants are exploring ways to provide visual indication, via the game itself, when the user goes off-axis, without requiring the user to close either eye. This would allow for self-correction by the player, without interrupting game play.

This third option is particularly interesting since it does not require any hardware changes or improved lenticular material. One possibility to generate the necessary feedback regarding screen angle relative to the player's head, without disturbing game play, is as follows. A border could be rendered around the edge of the screen, consisting of squares directed alternately to the left and right eye at the balance point contrast. When viewed by an amblyope (or person with anomalous binocular vision such as a strabismic) in the correct head position relative to the screen, the border would appear continuous. However, as their eyes move off-axis, the border would become a dashed line as the high contrast squares bleed over to the good eye, and lower contrast squares to the weaker eye. Note, however, that as the balance point moves closer to equality between the two eyes, this mechanism gradually loses its effectiveness.

Game designs. The fundamental element of the Tetris game is a square block. Different shapes are formed with this building block, and are sometimes referred to by the letter they resemble, as shown in FIG. 24.

Contrast difference: Each square block on the gameboard belongs to one of three categories, classified according to its contrast and visibility. The block contrast is defined by the relationship between the block and the background luminance in Equation 2. Visibility refers to whether a block is visible to the amblyopic eye only, the fellow eye only, or to both eyes. The three categories are:

High contrast blocks only visible to the amblyopic Eye
Low contrast blocks only visible to the fellow eye
Blocks visible to both eyes When starting the game for the first time, the contrast ratio value is determined empirically for each player using the dot stimulus method.

For Applicants initial experiment, Applicants presented blocks in the third contrast category to both eyes at an identical level of contrast. However, Applicants later realized that this approach risks having those blocks ignored by the amblyopic eye, in favor of the fellow eye. Applicants therefore modified these binocular blocks such as maximum contrast is seen by the amblyopic eye, while the fellow-eye contrast is at a value just above the balance point. This should ensure that the amblyopic eye remains engaged, but with the blocks still easy to see and track with both eyes cooperating.

2) Game Scoring and Difficulty-Level Adjustment:

Players may become disinterested in a computer game if it is not sufficiently challenging. For this reason, many games include a score display and dynamically adjust the difficulty level. In Tetris, a more difficult level typically means that the Tetris blocks fall faster. However, for Applicants platform, because much of the game information is divided between two eyes, the difficulty does not depend solely on the speed factor; it is also affected by how well the eyes cooperate at a given contrast ratio. Most importantly, the game difficulty increases when the interpreted signal by the brain is much fainter from one eye than the other.

While either of the mechanisms above may be employed to vary game difficulty, the former is strictly beneficial as means of maintaining player interest, while the latter optimizes the potential therapeutic effects. If, as the treatment progresses, the subject is able to play the game successfully with a reduced contrast difference between the two eyes, this represents an improvement over the initial condition. In order to both maintain player interest and achieve the maximum therapeutic effect, Applicants devised separate mechanisms for adjusting the game speed and contrast difference.

In Tetris, the score is based on the number of rows of Tetris blocks that have been removed from the gameboard. When a predetermined number of rows have been removed, the game speed is increased to a higher level of difficulty. Speed is specified by the number of seconds it takes for a block to fall the space of one row. Starting from an initial falling time of 700 ms/row, Applicants decrease this value by 50 ms every time the level advances. Eventually, the speed of the game may render it nearly impossible to play, and any therapeutic effect is lost. To prevent this from happening, game performance is monitored continuously. When the player fails to score in three consecutive games, the algorithm automatically reduces the existing speed by 50 ms per line.

Applicants did not have any prior data for this particular stimulus that might guide an automated inter-ocular contrast difference adjustment for maximal therapeutic benefit. Therefore, Applicants opted for a manual approach in Applicants initial experiment. Essentially, Applicants wanted the experimenters to use their judgement to move aggressively toward equal contrast between the eyes, while ensuring that game performance remains stable. The initial contrast difference is set to reflect the balanced-contrast condition, as measured during the dot stimulus experiment. The operator then reviewed the player's game performance each day, and based on consultation with the player, adjusted the contrast for the fellow eye upwards, thus moving closer to an equal-contrast condition and making the game more difficult for an amblyope to play.

Although not used in Applicants initial experiment, Applicants also implemented an automatic method for changing the interocular contrast difference between the two eyes. This is based on monitoring of game performance and decreasing the contrast difference by 5% after the player scores consistently high in a number of consecutive games, running at the same speed. The automatic adjustment would be repeated until the fellow-eye contrast reaches that of the amblyopic eye. Note that contrast difference and Tetris speed are never adjusted concurrently: the user plays at a given contrast level until their game performance is stable, then the contrast is adjusted to increase the difficulty. Since the game can be made more challenging without external intervention, such an automatic mechanism would be more appropriate for a commercial device, where visits to an optometrist may be infrequent.

Example 1

Game Design 1: Falling Tetris to one eye, ground rows to the other eye: The falling Tetris (at high-contrast) is directed to the amblyopic eye, while the stationary blocks on the ground are divided into two groups. The two top blocks of each column are rendered in low contrast and visible only to the fellow eye, while all remaining stationary blocks underneath are visible to both eyes in high contrast to provide a reference point to reduce spatial misalignment when matching monocularly-viewed game.

During a game of Tetris, the most relevant information comes from the shape of the falling Tetris and the pattern of the ground surface. Since this information is split between the two eyes, it must be combined to make the game playable. In addition to the shape information, the amblyopic eye has to track the Tetris' motion, while the presentation to the fellow eye remains stationary. This asymmetrical arrangement forces the amblyopic eye to work harder in the game, hopefully increasing any therapeutic effect.

Example 2

Game Design 2: Falling Tetris split between two eyes, ground rows equally to both eyes: For the second Design, each falling Tetris is split into three sections: one high-contrast section only visible to the amblyopic eye, one low-contrast section only visible to the good eye, and a middle section visible to both. All of the stationary blocks on the game board are also visible to both eyes and presented in high contrast.

This arrangement forces both eyes to follow the Tetris movement in order to see the complete shape. The purpose of having the central blocks of each Tetris visible to both eyes is to provide the player with an alignment cue, which helps to bridge the peripheral blocks that are only visible to a single eye. In an earlier prototype, Applicants divided the Tetris into two halves with each half exclusively seen by only one eye. This design introduced a misalignment effect in the Tetris shape, which was perceived by non-amblyopes even when the Tetris was stationary. The addition of the bridging portion helped alleviate this problem.

Example 3

Figure 27:
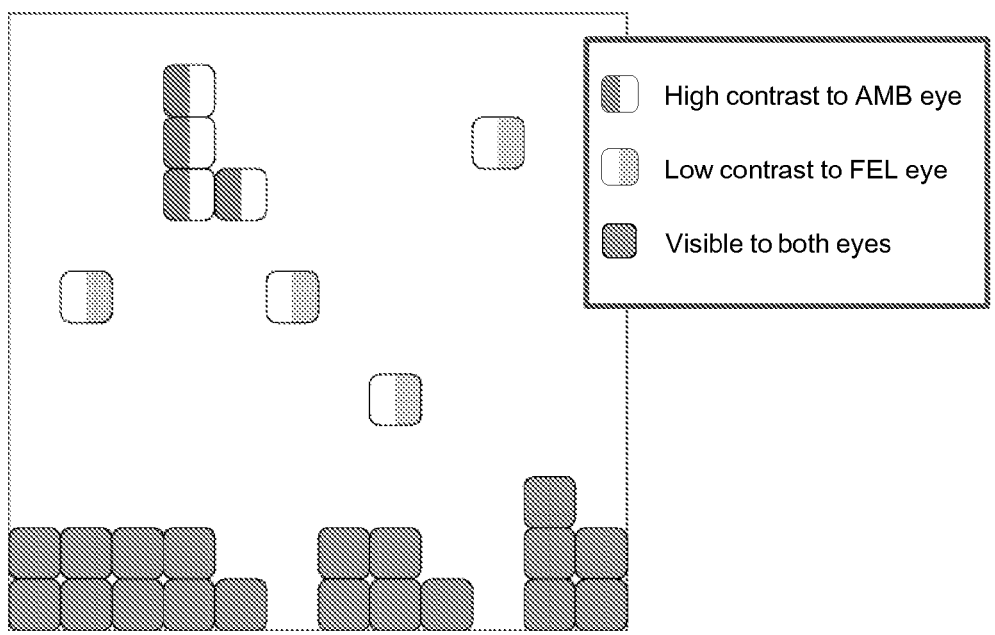
FIG. 27 shows mobile device for treating amblyopia with a camera-based anti-cheating system.

Game Design 3: All game information to amblyopic eye, random noise to fellow eye (see FIG. 27). In this approach, all the game information is directed only to the player's amblyopic eye and distractors are continuously presented to the fellow eye. Distractors are square blocks appearing during the game, with their locations randomized and updated approximately every 250 ms. This method was initially considered as part of the field trials, as it was most similar to the signal-to-noise paradigm used earlier in the dot stimulus protocol. This requires that the weaker eye attempt to detect the signal in the presence of noise presented to the fellow eye. However, Applicants abandoned this approach for a number of reasons. First, a player can cheat simply by closing the fellow eye, thereby eliminating the distractors. Second, from consultations with test subjects and Applicants own participation in these trials, it appears that the noise does not interfere significantly with the signal; because the random blocks are uncorrelated from frame to frame, they can easily be ignored by the fellow eye even while both eyes are open. While it is possible to increase the noise interference by raising the noise contrast and prevalence, this approach predictably makes the game much less enjoyable. More importantly, it does not encourage cooperation between the two eyes. Because the noise formation is irrelevant to the game, the incentive for the brain is to ignore the interference and see only the Tetris pieces. As a consequence, it might even trigger visual suppression of one eye to filter out the noise. Since an important goal of rehabilitation is to have the eyes working together, game content should therefore be constructed to elicit cooperation rather than suppression.

EXPERIMENT DESIGN AND EVALUATION OF OUTCOMES. Applicants might also be able to infer the user's degree of binocularity from the game scores directly, rather than by using a balance point measure such as the dot stimulus (does playing the game determine a balance point). However, as amblyopia is a visual disorder, a clinical assessment of the amblyopic condition is preferred to establish and monitor its severity from the start and throughout the experiment. In any case, an independent measure of amblyopia and binocular status is useful at least in the initial trials, since Applicants hope in the future to construct a self-adjusting game for rehabilitation through correlation between such data and the game performance. Thus, to monitor progress in the current experiment, Applicants interleave game sessions with regular measurements using the dot stimulus on the game device. In addition, Applicants measure the subject's balance point using a dot stimulus program running on a pair of goggles, which provides us with a reference measure completely independent from the iPod Touch device.

Experimental procedure. The experiment is being conducted by a team of vision experts in Departments of Opthalmology and Optometry. While Applicants leave many trial settings for the clinicians to decide, Applicants suggested the following procedure for running the test on each subject.

First Day:

1) Choose a game Design from the options described earlier. Each subject uses only a single Design throughout the entire experiment.

2) Allow the subject to play the game for five minutes to familiarize themselves with the game. All game elements are shown at high contrast to both eyes.

3) Measure subject's stereo and visual acuity

First Day, Every Five Days Thereafter, Plus Last Day:

1) Measure the subject's balance point on a goggle-based setup as an external reference to data gathered on the iPod Touch.

2) Go to the Daily procedure below, but only run the first set of three Tetris sessions (half the total amount played on days without the goggle measurement).

Daily:

1) Measure the balance point using the dot-stimulus experiment on the iPod Touch.

2) Set the appropriate balance point for the Tetris game based on the experimenter's knowledge of their previous game performance, the measured balance point, and how aggressively the experimenter wants to move towards equal contrast between the eyes. Note that if the experimenter moves too quickly, the player will not be able to effectively play the game, and their game performance should drop significantly, indicating that a more gradual shift is necessary.

3) Subject aligns the device relative to their head (held motionless in a chin rest) to ensure the correct signal is going to each eye, without significant bleeding.

4) Subject plays game for 15 minutes then takes a three minute break. Repeat three total times.

5) Ten minute break.

6) Subject plays game for 15 minutes then takes a three minute break. Repeat three total times.

7) Subject fills out questionnaire.

Results. Two pilot field tests were carried out concurrently by teams of ophthalmology and optometry researchers at McGill University in Montreal, Canada, and the University of Auckland in New Zealand, with a small number of volunteer subjects. This psychophysical experiment produced a number of encouraging observations.

First, at the beginning of the trial period, most amblyopic players required a contrast ratio strongly in favour of the weaker eye in order to play the game. Encouragingly, as the training sessions progressed, the subjects were able to play at progressively higher fellow eye contrasts, as desired. In general, the participants responded positively to the game format, suggesting that such treatment design is more engaging than a more traditional clinical treatment approach.

Visual acuity tests, conducted weekly, indicated improved acuity of the amblyopic eye for most of Applicants subjects (three out of four in the Auckland trial, and one out of two in Montreal). The Auckland trial also observed a small positive change in stereo vision for two of the subjects.

It should be noted that the current game design neither requires nor trains for stereo vision. Applicants envision that at a later stage of rehabilitation, a 3-D, Tetris-style game using a similar content-splitting strategy may provide more effective treatment for stereo deficiency.

The device of the present invention delivers the therapeutic effect by leveraging on the contrast imbalance to encourage the interocular cooperation between the eyes, hence making the amblyopic eye contribute actively to the visual system. The interactive content of the game format offers the potential to engage the patients over the treatment period, while also helping the eye-care practitioner monitor the progress based on contrast level from the game. Applicants received encouraging results from the early field tests, and expect that additional improvement to the current design will further enhance the usability and therapeutic effect of this device.

In comparison to the conventional practice of patching the good eye, the treatment of the present invention encourages the patients to observe and combine information using both eyes. As the binocular visual perception is balanced by means of differential contrasts across two eyes, treatment level can be monitored and advanced on a continuous basis towards the equal-contrast viewing condition. This also avoids cases of over-penalizing the fellow fixing eye, since binocular active vision is required to play the game. Naturally, an interactive game application is also more engaging to the patient than a passive exercise with visual stimuli.

The dichoptic display of the present invention can comprise a lenticular screen. One challenge of using a lenticular display is that it allows one to "cheat" (view both images with the strong eye) by varying the angle of view between the eyes and the device. In order to ensure proper use of the device, a camera can be provided with the device. The camera can track eye and/or head position or movement in order to ensure they are properly aligned such that the two eyes receive different images from the display screen. An analyzer receives this visual information from the camera and can stop or pause the game based on determination of a valid or non-valid eyes or head position.

Figure 28:
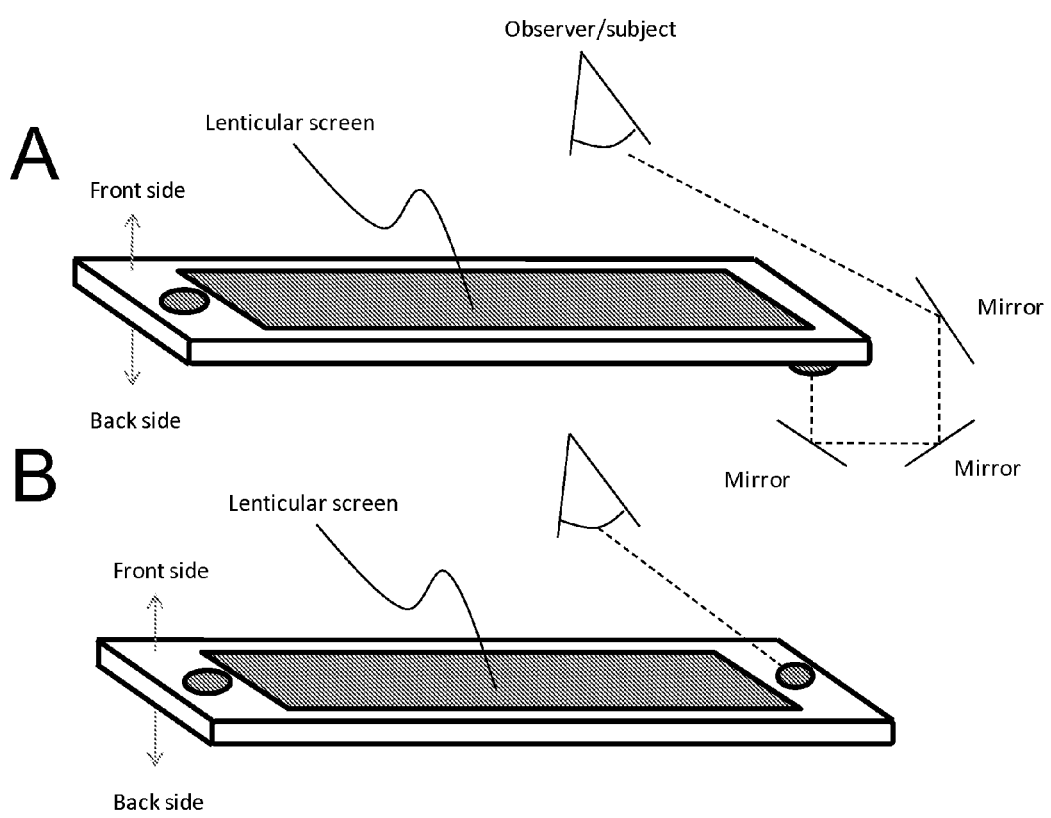
FIG. 28 shows a mobile device with proper use detector having a front-facing (8A) and a back-facing camera (8B).

It will be appreciated by those skilled in the art that a mobile device with a back-facing camera, can also be adapted with a system of mirrors (see FIG. 28), using for example an easy clip-on system to track a subject's eyes during a game. An "anti-cheating" device and a "proper use" device should be considered interchangeable and is important element when a lenticular material is used as a binocular separation device with a mobile device having a camera. It will be appreciated that, although this study uses an iPod Touch, the preferred embodiment has a display screen and a front facing camera for tracking eye movements (FIG. 28). A large number of mobile devices are provided with front facing cameras, including laptops, PDAs and mobile phones.

Other "proper use" mechanisms have been considered. For example, combining a tilt-sensor (accelerometer) inside the mobile device with camera view or head/neck restraint to maintain relative viewing angles can be used. As described above, using a boundary as visual feedback where adjacent segments are of alternative signal strengths can also provide an indication of proper use. When viewed from the proper viewing angle, the boundary appears as continuous. When viewed from an incorrect viewing angle, the boundary appears as disjointed. Another proper use mechanism uses explicit misalignment between non-overlapping game elements at the display level, along with a prism eye-glass at the eye level, to enforce a proper viewing angle. Finally, presenting the stimulus at a certain depth so that when the viewing angle is incorrect, the disparity causes distortions to the game element shapes, hence making the alignment task difficult to complete. Assigning different depths to different game elements, for example one depth for the moving Tetris and one depth level for the stationary grounded blocks can ensure proper use of the game for maximal efficiency. Another anti-cheating approach might simply be achieved by stereoscopically placing the game in a near-field plane such that without glasses, the objects appear blurred and with glasses, the objects appear to be crisp and in a plane in front of the screen.

The dichoptic display can comprise stereoscopic vision glasses to be worn by the patient, and the analyzer can determine if the patient is wearing the glasses. It will be understood that stereoscopic vision glasses for providing a binocular display can be any one of color glasses for anaglyphic, polarized lens glasses and shutter glasses.

The apparatus can be a handheld computing device with a front facing camera located on the housing of the display to image the patient looking as the display using the camera. It will be understood that a front-facing camera is a camera that is located on the same side of the apparatus as the display screen (as shown in FIG. 28).

The computing device has a stereoscopic lenticular screen overlay for stereoscopic viewing without stereoscopic glasses because it may be advantageous to provide a system that does not require external eye wear or head gear.

The computing device adjusts the images as a function of patient task performance in order to maintain treatment efficacy and player enjoyment. The game software can provide full contrast game objects to one eye and at least some reduced contrast game objects to another eye.

The computing device can adjust the images as function of patient task performance and can provide full contrast game objects to one eye and at least some reduced contrast game objects to another eye.

Although the game used by Applicants is a Tetris game, it will be appreciated that any game able to present and separate visual information at a more elementary level would be useful. Indeed, such a game requires low level cortical integration of information content as opposed to some games which require high level cortical integration such as a racing game or a first person shooter game. In these latter two types of games, the higher cortical regions are required to process and integrate complex visual cues relating to environment, relationships, etc.

Another example of a game (in this case a task) adapted for low level cortical integration is the random-dot kinematogram shown in FIG. 18. This game, and many others that can be adapted for separation of visual information at a local level and consistent throughout a field, are useful for treating binocular disorders.

One of many advantages of using a mobile device is the automatic synchronization of longitudinal data (performance results that can be based on Tetris falling speed, number of rows completed, contrast, etc) with an eye care specialist over a network (cellular network or internet, depending on the type of mobile device). This transmission, combined to the fact that playing a game on a mobile device is an enjoyable task that can be performed anywhere, makes for enhanced patience compliance. This is important for younger patients.

Information exchange between the mobile device and doctor's office on game performance and contrast settings allow health care practitioners to direct the treatment progress remotely, hence reducing or avoiding the physical patient visits. This system allows for remote diagnosis of stereopsis/binocular vision deficiencies. Furthermore, the eye-tracking data from built-in camera and analyzer can allow for measuring the stability of vergence movement across the eyes, important where there are imbalances to the eye muscles. Finally, using eye-tracking data from built-in camera can allow to monitor eye movements during the game to infer on oculomotor imbalance for persons with strabismus/binocular vision anomalies.

Applicant's objective was to develop a game that delivers as much therapeutic effect as possible, while keeping the game engaging to the player. Applicants provide a method to adjust the difficulty of the game automatically, based on performance of the player, with the objective of further improving the therapeutic effects. An algorithm assigns the differential contrasts to the game elements to continuously move viewing towards an equal-contrast condition (i.e adjusting the balance point), while at the same time maintaining a challenging game speed the player.

REFERENCES

Baker, D. H., Meese, T. S., & Summers, R. J. (2007). Psychophysical evidence for two routes to suppression before binocular summation of signals in human vision. *Neuroscience,* 146 (1), 435-448.

Braddick, O. (1974). A short-range process in apparent motion. *Vision Res,* 14 (7), 519-527.

Brainard, D. H. (1997). The Psychophysics Toolbox. *Spatial Vision,* 10 (4), 433-436.

Campbell, F. W., & Green, D. G. (1965). Monocular versus binocular visual acuity. *Nature,* 208 (5006), 191-192.

Crawford, M. L., & von Noorden, G. K. (1979). The effects of short-term experimental strabismus on the visual system in Macaca mulatta. *Invest Opthalmol Vis Sci,* 18 (5), 496-505.

Edwards, M., & Badcock, D. R. (1995). Global motion perception: No interaction between the first- and second-order pathways. *Vision Research,* 35 (18), 2589-2602.

Foster, D. H., & Bischop, W. F. (1997). Bootstrap estimates of the statistical accuracy of thresholds obtained from psychometric functions. *Spatial Vision,* 11 (1), 135-139. Harrad, R., Sengpiel, F., & Blakemore, C. (1996). Physiology of suppression in strabismic amblyopia. *Br J Opthalmol,* 80 (4), 373-377.

Hess, R. F., Hutchinson, C. V., Ledgeway, T., & Mansouri, B. (2007). Binocular influences on global motion processing in the human visual system. *Vision Res,* 47 (12), 1682-1692.

Hubel, D. H., & Wiesel, T. N. (1965). Binocular interaction in striate cortex of kittens reared with artificial squint. *Journal of Neurophysiology,* 28 (6), 1041-1059.

King-Smith, P. E., & Rose, D. (1997). Principles of an adaptive method for measuring the slope of the psychometric function. *Vision Research,* 37 (12), 1595-1604.

Kiorpes, L., Kiper, D. C., O'Keefe, L. P., Cavanaugh, J. R., & Movshon, J. A. (1998). Neuronal correlates of amblyopia in the visual cortex of macaque monkeys with experimental strabismus and anisometropia. *Journal of Neuroscience,* 18 (16), 6411-6424.

Levi, D. M., Pass, A. F., & Manny, R. E. (1982). Binocular interactions in normal and anomalous binocular vision: effects of flicker. *Br J Opthalmol,* 66 (1), 57-63.

Mansouri, B., Allen, H. A., Hess, R. F., Dakin, S. C., & Ehrt, O. (2004). Integration of orientation information in amblyopia. *Vision Research,* 44 (25), 2955-2969.

Mansouri, B., Hess, R. F., Allen, H. A., & Dakin, S. C. (2005). Integration, segregation, and binocular combination. *Journal of Optical Society of America A: Optics, Image Sciences, and Vision,* 22 (1), 38-48.

McKee, S. P., Levi, D. M., & Movshon, J. A. (2003). The pattern of visual deficits in amblyopia. *J Vis,* 3 (5), 380-405.

Meese, T. S., Georgeson, M. A., & Baker, D. H. (2006). Binocular contrast vision at and above threshold. *J Vis,* 6 (11), 1224-1243.

Mitchell, D. E., Howell, E. R., & Keith, C. G. (1983). The effect of minimal occlusion therapy on binocular visual functions in amblyopia. *Invest Opthalmol Vis Sci,* 24 (6), 778-781.

Newsome, W. T., Britten, K. H., Salzman, C. D., & Movshon, J. A. (1990). Neuronal mechanisms of motion perception. *Cold Spring Harb Symp Quant Biol,* 55, 697-705.

Newsome, W. T., & Pare, E. B. (1988). A selective impairment of motion perception following lesions of the middle temporal visual area (MT). *Journal of Neuroscience,* 8 (6), 2201-2211.

Pelli, D. G. (1997). The VideoToolbox software for visual psychophysics: transforming numbers into movies. *Spatial Vision,* 10 (4), 437-442.

Pelli, D. G., & Zhang, L. (1991). Accurate control of contrast on microcomputer displays. *Vision Research,* 31 (7-8), 1337-1350.

Rosenbach, O. (1903). Ueber monokulare Vorherrschaft beim binikularen Sehen. *Munchener Medizinische Wochenschriff,* 30, 1290-1292.

Sengpiel, F., & Blakemore, C. (1996). The neural basis of suppression and amblyopia in strabismus. *Eye,* 10 (Pt 2), 250-258.

Sengpiel, F., Blakemore, C., Kind, P. C., & Harrad, R. (1994). Interocular suppression in the visual cortex of strabismic cats. *J Neurosci,* 14 (11 Pt 2), 6855-6871.

Sengpiel, F., Freeman, T. C., & Blakemore, C. (1995). Interocular suppression in cat striate cortex is not orientation selective. *Neuroreport,* 6 (16), 2235-2239.

Vedamurthy, I., Suttle, C. M., Alexander, J., & Asper, L. J. (2007). Interocular interactions during acuity measurement in children and adults, and in adults with amblyopia. *Vision Res,* 47 (2), 179-188.

Watt, R. J., & Andrews, D. (1981). APE. Adaptive Probit estimation of the psychometric function. *Current Psychological Review,* 1, 205-214.

Wurtz, R. H., & Kandel, E. R. (2004). Motion and Form Perception. In: E. R. Kandel (Ed.) *Principles of Neuroscience* (p. 584).

What is claimed is:

1. A binocular vision assessment and/or therapy apparatus comprising:
a source of left eye image and right eye image pairs adapted to be viewed dichoptically and perceived with binocular vision, said pairs having a variable difference between said left eye image and said right eye image;
a dichoptic display system presenting a selected one of said images pairs as a right eye image to a patient's right eye and a left eye image to a patient's left eye; and
a proper use detector having a camera for imaging a patient using said dichoptic display system and an image analyzer for determining proper use of said display system by the patient.

2. The apparatus as claimed in claim 1, wherein the dichoptic display comprises a lenticular screen, and said analyzer determines proper position of the patient with respect to the screen.

3. The apparatus as claimed in claim 1, wherein the dichoptic display comprises stereoscopic vision glasses to be worn by the patient, and said analyzer determines if the patient is wearing said glasses.

4. The apparatus as claimed in claim 1, wherein said camera is mounted to be solid with a screen of said display system.

5. The apparatus as claimed in claim 4, wherein said apparatus comprises a handheld computing device, said camera is located on a housing of said display to image in a front-facing direction of said display, further comprising a optical device for imaging said patient looking as said display using said camera.

6. A binocular vision assessment and/or therapy apparatus comprising:
a handheld computing device having game software defining a task to be performed by a patient by interaction with the device, the software including a source of left eye image and right eye image pairs adapted to be viewed dichoptically and perceived with binocular vision, said pairs having a variable difference between said left eye image and said right eye image; and
said computing device being adapted to present a selected one of said images pairs as a right eye image to a patient's right eye and a left eye image to a patient's left eye, wherein said software records patient task performance and synchronizes task performance data collected over time with a data network for access by a health care professional.

7. The apparatus as claimed in claim 6, wherein computing device has a stereoscopic lenticular screen overlay for stereoscopic viewing without stereoscopic glasses.

8. The apparatus as claimed in claim 6, wherein said computing device adjusts said images as function of patient task performance.

9. The apparatus as claimed in claim 6, wherein said game software provides full contrast game objects to one eye and at least some reduced contrast game objects to another eye.

10. The apparatus as claimed in claim 6, wherein said game software provides a task comprises elementary level separation of visual information requiring low level cortical integration.

11. The apparatus as claimed in claim 9, wherein said game software provides a Tetris-style game.

12. A binocular vision assessment and/or therapy apparatus comprising:
a handheld computing device having a stereoscopic lenticular screen overlay for stereoscopic viewing without stereoscopic glasses and game software defining a task to be performed by a patient by interaction with the device, the software including a source of left eye image and right eye image pairs adapted to be viewed dichoptically and perceived with binocular vision, said pairs having a variable difference between said left eye image and said right eye image; and
said computing device being adapted to present a selected one of said images pairs as a right eye image to a patient's right eye and a left eye image to a patient's left eye.

13. The apparatus as claimed in claim 12, wherein said computing device adjusts said images as function of patient task performance.

14. The apparatus as claimed in claim 12, wherein said game software provides full contrast game objects to one eye and at least some reduced contrast game objects to another eye.

15. The apparatus as claimed in claim 12, wherein said game software provides a task comprises elementary level separation of visual information requiring low level cortical integration.

16. The apparatus as claimed in claim 15, wherein said game software provides a Tetris-style game.

* * * * *